United States Patent
Liu et al.

(10) Patent No.: US 10,449,250 B2
(45) Date of Patent: Oct. 22, 2019

(54) ANTI-SCLEROSTIN ANTIBODY, ANTIGEN BINDING FRAGMENT AND MEDICAL USE THEREOF

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Jiajian Liu, Shanghai (CN); Yayuan Fu, Shanghai (CN); Haoying Zhang, Shanghai (CN); Yifang Wang, Shanghai (CN); Zhen Zhang, Shanghai (CN); Ling Zhang, Shanghai (CN); Dongbing Cui, Shanghai (CN); Lianshan Zhang, Shanghai (CN); Weikang Tao, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 15/556,488

(22) PCT Filed: Feb. 16, 2016

(86) PCT No.: PCT/CN2016/073857
§ 371 (c)(1),
(2) Date: Sep. 7, 2017

(87) PCT Pub. No.: WO2016/145961
PCT Pub. Date: Sep. 22, 2016

(65) Prior Publication Data
US 2018/0099046 A1 Apr. 12, 2018

(30) Foreign Application Priority Data
Mar. 13, 2015 (CN) .......................... 2015 1 0112924

(51) Int. Cl.
| | | |
|---|---|---|
| A61K 39/395 | (2006.01) |
| C07K 16/18 | (2006.01) |
| A61P 19/08 | (2006.01) |
| A61P 1/02 | (2006.01) |
| A61P 19/02 | (2006.01) |
| A61P 19/10 | (2006.01) |
| A61K 48/00 | (2006.01) |
| C12N 15/63 | (2006.01) |
| C07K 16/22 | (2006.01) |
| A61K 39/00 | (2006.01) |

(52) U.S. Cl.
CPC ...... *A61K 39/39533* (2013.01); *A61K 48/005* (2013.01); *A61P 1/02* (2018.01); *A61P 19/02* (2018.01); *A61P 19/10* (2018.01); *C07K 16/18* (2013.01); *C07K 16/22* (2013.01); *C12N 15/63* (2013.01); *A61K 2039/505* (2013.01); *C07K 2317/24* (2013.01); *C07K 2317/51* (2013.01); *C07K 2317/515* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2007/0072797 A1* 3/2007 Robinson ............... C07K 14/51
424/185.1

FOREIGN PATENT DOCUMENTS

| | | |
|---|---|---|
| CN | 101646457 A | 2/2010 |
| CN | 103435698 A | 12/2013 |
| WO | 2006119107 A2 | 11/2006 |
| WO | 2008115732 A2 | 9/2008 |
| WO | 2008133722 A2 | 11/2008 |

OTHER PUBLICATIONS

Knappik et al., J. Mol. Biol., 2000, vol. 296(1):57-86.*
Rudikoff et al., Proc. Natl. Acad. Sci, USA, 1982, vol. 79:1979-1983.*
Int'l Search Report dated May 20, 2016 in Int'l Application No. PCT/CN2016/073857.
"IUPAC-IUB Commission on Biochemical Nomenclature A One-Letter Notation for Amino Acid Sequences Tentative Rules," The Journal of Biological Chemistry, vol. 243, No. 13, pp. 3557-3559 (1968).
Queen et al, "Humanized Antibodies for Antiviral Therapy," Proc. Natl. Acad. Sci. USA, vol. 88, pp. 2869-2873 (1991).
Jones et al, "Replacing the Complimentarity-Determining Regions in a Human Antibody With Those From a Mouse," Nature, vol. 321, pp. 522-525 (1986).
Riechmann et al, "Reshaping Human Antibodies for Therapy," Nature, vol. 332, pp. 323-327 (1988).
Verhoeyen et al, "Reshaping Human Antibodies: Grafting an Antilysozyme Activity," Science, vol. 239, No. 4847, pp. 1534-1536 (1988).

* cited by examiner

*Primary Examiner* — Xiaozhen Xie
(74) *Attorney, Agent, or Firm* — Panitch Schwarze Belisario & Nadel LLP

(57) ABSTRACT

Provided is a humanized antibody and chimeric antibody that specifically binds human sclerostin. The antibodies can be used for treating human bone metabolism related diseases such as osteoporosis (OP).

20 Claims, 1 Drawing Sheet
Specification includes a Sequence Listing.

SEQUENCE LISTING

```
<160> NUMBER OF SEQ ID NOS: 29

<210> SEQ ID NO 1
<211> LENGTH: 657
<212> TYPE: DNA
<213> ORGANISM: artificial sequence
<220> FEATURE:
<223> OTHER INFORMATION: DNA sequence encoding human sclerostin with
      Histag (His-h-SOST)

<400> SEQUENCE: 1
atggacatga gggtgcctgc ccaactgctg ggcctgttgt tgctttggtt ccccggaagc      60
aggtgccatc atcaccacca tcatcagggc tggcaggcct tcaagaacga cgcaaccgag     120
attatccccg aactgggcga atatcccgag cccctccag agctggagaa taacaagacc      180
atgaacaggg ccgagaacgg cggcagaccc ccccatcatc ccttcgagac taaagacgtg     240
agcgagtaca gctgcaggga gctgcatttc accaggtacg tgaccgatgg ccctgtagg     300 agcgccaagc ccgtgactga actggtgtgc agcggccagt gcggtccggc cagactgctg     360
ccgaacgcta tcggcagggg caagtggtgg aggccctctg acccgactt caggtgcata     420 cccgacaggt accgcgctca gagagtgcaa ctgttgtgtc ctgggggcga ggctccgagg     480
gcgcgaaagg tgaggctggt ggccagttgt aagtgcaaga ggctgaccag gttccacaac     540
cagagcgagc tgaaggactt cggcaccgaa gcagccaggc cgcagaaggg caggaagccc     600
aggccacgag cacgatccgc caaagccaat caggcagagc tcgagaatgc ctactga       657

<210> SEQ ID NO 2
<211> LENGTH: 663
<212> TYPE: DNA
<213> ORGANISM: artificial sequence
<220> FEATURE:
<223> OTHER INFORMATION: DNA sequence encoding human sclerostin with
      Flagtag (h-SOST-Flag)

<400> SEQUENCE: 2
atggacatga gggtgcctgc ccaactgctg ggcctgttgt tgctttggtt ccccggaagc      60
aggtgccagg gctggcaggc cttcaagaac gacgcaaccg agattatccc cgaactgggc     120
gaatatcccg agccccctcc agagctggag aataacaaga ccatgaacag ggccgagaac     180
ggcggcagac ccccccatca tcccttcgag actaaagacg tgagcgagta cagctgcagg     240
gagctgcatt tcaccaggta cgtgaccgat ggcccctgta ggagcgccaa gcccgtgact     300
gaactggtgt gcagcggcca gtgcggtccg gccagactgc tgccgaacgc tatcggcagg     360
ggcaagtggt ggaggccctc tgacccgac ttcaggtgca tacccgacag gtaccgcgct      420
cagagagtgc aactgttgtg tcctgggggc gaggctccga gggcgcgaaa ggtgaggctg     480
gtggccagtt gtaagtgcaa gaggctgacc aggttccaca accagagcga gctgaaggac     540
ttcggcaccg aagcagccag gccgcagaag ggcaggaagc caggccacga gcacgatcc     600 gccaaagcca atcaggcaga gctcgagaat gcctacgact acaaggatga cgacgacaag     660
tga                                                                   663
```

<210> SEQ ID NO 3
<211> LENGTH: 657
<212> TYPE: DNA
<213> ORGANISM: artificial sequence
<220> FEATURE:
<223> OTHER INFORMATION: DNA sequence encoding mouse sclerostin with
      Flagtag (m-SOST-Flag)

<400> SEQUENCE: 3

```
atggacatga gggtgcctgc ccaactgctg ggcctgttgt tgcttttggtt ccccggaagc    60
aggtgccagg gctggcaggc cttcaggaac gacgcaaccg aggtgatccc cggactgggc   120
gaatatcccg agccccctcc agagaataac cagaccatga cagggccgga aacggcggc    180
agaccccccc atcatcccta cgacgctaaa ggcgtgagcg agtacagctg cagggagctg   240
cattacacca ggttcctgac cgatggcccc tgtaggagcg ccaagcccgt gactgaactg   300
gtgtgcagcg ccagtgcgg tccggccaga ctgctgccga acgctatcgg cagggtcaag   360
tggtggaggc ccaacggacc cgacttcagg tgcataccccg acaggtaccg cgctcagaga   420
gtgcaactgt tgtgtcctgg gggcgccgct ccgaggagcc gaaaggtgag gctggtggcc   480
agttgtaagt gcaagaggct gaccaggttc acaaccaga gcgagctgaa ggacttcggc   540
cccgaaacag ccaggccgca gaagggcagg aagcccaggc caggagcacg aggagccaaa   600
gccaatcagg cagagctcga gaatgcctac gactacaagg atgacgacga caagtga      657
```

<210> SEQ ID NO 4
<211> LENGTH: 663
<212> TYPE: DNA
<213> ORGANISM: artificial sequence
<220> FEATURE:
<223> OTHER INFORMATION: DNA sequence encoding cyno sclerostin with
      Flagtag(cyno-SOST-Flag)

<400> SEQUENCE: 4

```
atggacatga gggtgcctgc ccaactgctg ggcctgttgt tgcttttggtt ccccggaagc    60
aggtgccagg gctggcaggc cttcaagaac gacgcaaccg agattatccc cgaactgggc   120
gaatatcccg agccccctcc agagctggag aataacaaga ccatgaacag ggccgagaac   180
ggcggcagac ccccccatca tcccttcgag actaaagacg tgagcgagta cagctgcagg   240
gagctgcatt tcaccaggta cgtgaccgat ggccagtgta ggagcgccaa gcccgtgact   300
gaactggtgt gcagcggcca gtgcggtccg ccagactgc tgccgaacgc tatcggcagg   360
ggcaagtggt ggaggccctc tggacccgac ttcaggtgca tacccgacag gtaccgcgct   420
cagagagtgc aactgttgtg tcctgggggc gccgctccga gggcgcgaaa ggtgaggctg   480
gtggccagtt gtaagtgcaa gaggctgacc aggttccaca accagagcga gctgaaggac   540
ttcggccccg aagcagccag gccgcagaag ggcaggaagc ccaggccacg agcacgagga   600
gccaaagcca atcaggcaga gctcgagaat gcctacgact acaaggatga cgacgacaag   660
tga                                                                  663
```

<210> SEQ ID NO 5
<211> LENGTH: 117
<212> TYPE: PRT
<213> ORGANISM: murine

<400> SEQUENCE: 5

Glu Val Gln Leu Gln Gln Ser Gly Pro Glu Leu Val Lys Pro Gly Thr
1               5                   10                  15

```
Ser Val Lys Ile Pro Cys Gln Thr Ser Gly Tyr Thr Phe Thr Asp Tyr
            20                  25                  30

Asn Leu Asp Trp Leu Lys Gln Arg Pro Gly Glu Ser Leu Glu Trp Ile
        35                  40                  45

Gly Asp Ile Asp Pro Asn Asn Gly Asp Ile Leu Tyr Asn Gln Lys Phe
 50                  55                  60

Arg Asp Lys Ala Thr Leu Thr Val Asp Thr Ser Ser Asn Thr Ala Tyr
 65                  70                  75                  80

Leu Glu Leu Arg Ser Leu Thr Ser Glu Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Leu Thr Ile Ser Ser
        115

<210> SEQ ID NO 6
<211> LENGTH: 107
<212> TYPE: PRT
<213> ORGANISM: Murine

<400> SEQUENCE: 6

Asn Ile Val Met Thr Gln Thr Pro Lys Leu Leu Phe Val Ser Ala Gly
1               5                   10                  15

Asp Arg Ile Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Thr Ser Asn Arg Phe Thr Gly Val Pro Asp Arg Phe Thr Gly
 50                  55                  60

Ser Gly Tyr Gly Thr Asp Phe Thr Leu Thr Ile Asn Thr Val Gln Ala
65                  70                  75                  80

Glu Asp Leu Ala Val Tyr Phe Cys Gln Gln Asp Tyr Ser Ser Pro Val
                85                  90                  95

Thr Phe Gly Ala Gly Thr Lys Leu Glu Leu Lys
            100                 105

<210> SEQ ID NO 7
<211> LENGTH: 5
<212> TYPE: PRT
<213> ORGANISM: Murine

<400> SEQUENCE: 7

Asp Tyr Asn Leu Asp
1               5

<210> SEQ ID NO 8
<211> LENGTH: 17
<212> TYPE: PRT
<213> ORGANISM: Murine

<400> SEQUENCE: 8

Asp Ile Asp Pro Asn Asn Gly Asp Ile Leu Tyr Asn Gln Lys Phe Arg
1               5                   10                  15

Asp

<210> SEQ ID NO 9
<211> LENGTH: 8
<212> TYPE: PRT
```

```
<213> ORGANISM: Murine

<400> SEQUENCE: 9

Arg Trp Ala Tyr Tyr Phe Asp Tyr
1               5

<210> SEQ ID NO 10
<211> LENGTH: 11
<212> TYPE: PRT
<213> ORGANISM: Murine

<400> SEQUENCE: 10

Lys Ala Ser Gln Ser Val Ser Asn Asp Val Ala
1               5                   10

<210> SEQ ID NO 11
<211> LENGTH: 7
<212> TYPE: PRT
<213> ORGANISM: Murine

<400> SEQUENCE: 11

Tyr Thr Ser Asn Arg Phe Thr
1               5

<210> SEQ ID NO 12
<211> LENGTH: 9
<212> TYPE: PRT
<213> ORGANISM: Murine

<400> SEQUENCE: 12

Gln Gln Asp Tyr Ser Ser Pro Val Thr
1               5

<210> SEQ ID NO 13
<211> LENGTH: 17
<212> TYPE: PRT
<213> ORGANISM: artificial sequence
<220> FEATURE:
<223> OTHER INFORMATION: HCDR2 Mutant

<400> SEQUENCE: 13

Asp Ile Asp Pro Asn Asp Gly Asp Ile Leu Tyr Asn Gln Lys Phe Arg
1               5                   10                  15

Asp

<210> SEQ ID NO 14
<211> LENGTH: 117
<212> TYPE: PRT
<213> ORGANISM: artificial sequence
<220> FEATURE:
<223> OTHER INFORMATION: Heavy chain variable region of Ab-5

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Val Arg Gln Ala Pro Gly Gln Gly Leu Glu Trp Met
        35                  40                  45

Gly Asp Ile Asp Pro Asn Asn Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80
```

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser
        115

<210> SEQ ID NO 15
<211> LENGTH: 117
<212> TYPE: PRT
<213> ORGANISM: artificial sequence
<220> FEATURE:
<223> OTHER INFORMATION: Heavy chain variable region of Ab-9

<400> SEQUENCE: 15

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Leu Arg Gln Ala Pro Gly Glu Gly Leu Glu Trp Ile
        35                  40                  45

Gly Asp Ile Asp Pro Asn Asn Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser
        115

<210> SEQ ID NO 16
<211> LENGTH: 117
<212> TYPE: PRT
<213> ORGANISM: artificial sequence
<220> FEATURE:
<223> OTHER INFORMATION: Heavy chain variable region of Ab-10

<400> SEQUENCE: 16

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Leu Arg Gln Ala Pro Gly Glu Gly Leu Glu Trp Ile
        35                  40                  45

Gly Asp Ile Asp Pro Asn Asp Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser
        115

-continued

```
<210> SEQ ID NO 17
<211> LENGTH: 107
<212> TYPE: PRT
<213> ORGANISM: artificial sequence
<220> FEATURE:
<223> OTHER INFORMATION: Light chain variable region of Ab-5

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Thr Ser Asn Arg Phe Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Val
                85                  90                  95

Thr Phe Gly Gly Gly Thr Lys Val Glu Ile Lys
            100                 105

<210> SEQ ID NO 18
<211> LENGTH: 107
<212> TYPE: PRT
<213> ORGANISM: artificial sequence
<220> FEATURE:
<223> OTHER INFORMATION: Light chain variable region of Ab-9

<400> SEQUENCE: 18

Asn Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45

Tyr Tyr Thr Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Val
                85                  90                  95

Thr Phe Gly Gly Gly Thr Lys Val Glu Ile Lys
            100                 105

<210> SEQ ID NO 19
<211> LENGTH: 107
<212> TYPE: PRT
<213> ORGANISM: artificial sequence
<220> FEATURE:
<223> OTHER INFORMATION: Light chain variable region of Ab-10

<400> SEQUENCE: 19

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45
```

```
Tyr Tyr Thr Ser Asn Arg Phe Thr Gly Val Pro Asp Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Asp Tyr Ser Ser Pro Val
                 85                  90                  95

Thr Phe Gly Gly Gly Thr Lys Val Glu Ile Lys
            100                 105

<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
```

Leu Ser Leu Ser Leu Gly
            325

<210> SEQ ID NO 21
<211> LENGTH: 327
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 22
<211> LENGTH: 330

```
<212> TYPE: PRT
<213> ORGANISM: Homo sapiens

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 107
<212> TYPE: PRT
<213> ORGANISM: Homo sapiens

<400> SEQUENCE: 23

Arg Thr Val Ala Ala Pro Ser Val Phe Ile Phe Pro Pro Ser Asp Glu
1               5                   10                  15
```

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 24
<211> LENGTH: 447
<212> TYPE: PRT
<213> ORGANISM: artificial sequence
<220> FEATURE:
<223> OTHER INFORMATION: Humanized antibody heavy chain of Ab-10

<400> SEQUENCE: 24

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Val Arg Gln Ala Pro Gly Gln Gly Leu Glu Trp Met
        35                  40                  45

Gly Asp Ile Asp Pro Asn Asn Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

```
Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 25
<211> LENGTH: 444
<212> TYPE: PRT
<213> ORGANISM: artificial sequence
<220> FEATURE:
<223> OTHER INFORMATION: Humanized antibody heavy chain of Ab-9

<400> SEQUENCE: 25

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Leu Arg Gln Ala Pro Gly Glu Gly Leu Glu Trp Ile
        35                  40                  45

Gly Asp Ile Asp Pro Asn Asn Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190
```

```
Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
    355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 26
<211> LENGTH: 443
<212> TYPE: PRT
<213> ORGANISM: artificial sequence
<220> FEATURE:
<223> OTHER INFORMATION: Humanized antibody heavy chain of Ab-5

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu Asp Trp Leu Arg Gln Ala Pro Gly Glu Gly Leu Glu Trp Ile
        35                  40                  45

Gly Asp Ile Asp Pro Asn Asp Gly Asp Ile Leu Tyr Asn Gln Lys Phe
    50                  55                  60

Arg Asp Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Arg Trp Ala Tyr Tyr Phe Asp Tyr Trp Gly Gln Gly Thr Thr
            100                 105                 110
```

```
Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 27
<211> LENGTH: 214
<212> TYPE: PRT
<213> ORGANISM: artificial sequence
<220> FEATURE:
<223> OTHER INFORMATION: Humanized antibody light chain of Ab-10

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30
```

Val Ala Trp Tyr Gln Gln Lys Pro Gly Lys Ala Pro Lys Leu Leu Ile
                35                  40                  45

Tyr Tyr Thr Ser Asn Arg Phe Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asp Tyr Ser Ser Pro Val
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 214
<212> TYPE: PRT
<213> ORGANISM: artificial sequence
<220> FEATURE:
<223> OTHER INFORMATION: Humanized antibody light chain of Ab-9

<400> SEQUENCE: 28

Asn Ile Val Met Thr Gln Ser Pro Ser Ser Leu Ser Ala Ser Val Gly
 1               5                  10                  15

Asp Arg Val Thr Ile Thr Cys Lys Ala Ser Gln Ser Val Ser Asn Asp
                 20                  25                  30

Val Ala Trp Tyr Gln Gln Lys Pro Gly Lys Ser Pro Lys Leu Leu Ile
                35                  40                  45

Tyr Tyr Thr Ser Asn Arg Phe Thr Gly Val Pro Asp Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Asp Tyr Ser Ser Pro Val
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 214
<212> TYPE: PRT
<213> ORGANISM: artificial sequence
<220> FEATURE:
<223> OTHER INFORMATION: Humanized antibody light chain of Ab-5

<400> SEQUENCE: 29

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ser Pro Lys Leu Leu Ile
        35                  40                  45

Tyr Tyr Thr Ser Asn Arg Phe Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Asp Tyr Ser Ser Pro Val
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-SCLEROSTIN ANTIBODY, ANTIGEN BINDING FRAGMENT AND MEDICAL USE THEREOF

CROSS-REFERENCE TO RELATED APPLICATION

This application is a Section 371 of International Application No. PCT/CN2016/073857, filed Feb. 16, 2016, which was published in the Chinese language on Sep. 22, 2016 under International Publication No. WO 2016/145961 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing 688452_52US", creation date of Sep. 5, 2017, and having a size of 41.3 KB. The sequence listing submitted via EFS-Web is part of the specification and is herein incorporated by reference in its entirety.

FIELD OF THE INVENTION

The present invention relates to an antibody that specifically binds to human sclerostin (SOST) with high affinity, and an antigen-binding fragment thereof, as well as use of the antibody as a therapeutic agent, especially for SOST-mediated bone diseases or disorders such as osteoporosis, wherein the subject benefits from an increase in at least one of bone mass, bone mineral density, bone mineral content, and bone strength.

BACKGROUND OF THE INVENTION

Osteoporosis (OP), including postmenopausal Osteoporosis (PMO) and senile osteoporosis, is a systemic disorder of bone metabolism, characterized by low bone mass and degradation of bone microstructure, resulting in decreased bone strength, increased bone fragility, and susceptibility to fracture. According to statistics, about 200 million people in the world suffer from osteoporosis, and the incidence rose into the top seven most common diseases and frequently occurring diseases. The prevalence rate of osteoporosis in Chinese females over 60 years old is as high as 60%, and the prevalence rate for males is also 40-50%.

In addition to strengthening exercise, taking calcium and vitamin D, the spread of knowledge for fracture prevention and other traditional measures, the current medical treatment is mainly limited to reducing bone absorption to prevent fracture. The anti-bone absorption drugs include calcitonin, bisphosphonates, estrogen replacement agents and selective estrogen receptor modulators (SERMs), etc. These bone absorption inhibitors, which are represented by bisphosphonates, can prevent further bone loss, but fail to reconstruct the lost bone. Also, these bone absorption inhibitors fail to inhibit osteogenesis while inhibiting bone absorption. Hormonal drugs have more risks and are associated with venous thrombosis and cardiovascular disease. More importantly, bone anabolic drugs, in their true sense, not only improve bone mass, but also effectively improve the bone microstructure and promote osteogenesis. However, this is precisely what the existing anti-bone absorption drugs cannot do. In the past 15 years, various medical measures aiming at reducing fracture risk have been systematically investigated in clinical trials, while the actual available drugs are still quite limited. So far, only parathyroid hormone (PTH) drugs have been proven to stimulate osteogenesis. However, many disadvantages are known. For example, it is not a lasting solution for the purpose of bone remodeling and has little effect on fracture repair. It also needs to be percutaneously administered every day for more than one year, and only administered in a low-dose; is high cost and cannot be continuously used for more than two years; and its safety exposure resulted in a black-box warning from the US FDA, etc.

Sclerostin serves as a new biological target for drug development, and the principle is that osteoporosis could be treated by regulating anabolism of osteoblasts. Such a target fills a gap in the field of treating osteoporosis by regulating bone metabolism.

Sclerostin is a secretory glycoprotein expressed by the SOST gene, and its amino acid sequence is characterized by 190 residues and a hoop domain containing cysteine. It has been shown that it is mainly expressed in bone cells, with very low expression in osteoblasts, cartilage, liver, kidney, bone marrow, heart, pancreas and other locations.

Studies have shown that sclerotin can regulate osteogenesis through inhibiting the Wnt signaling pathway by binding to low-density lipoprotein receptor LRP5/6. At present, monoclonal antibody drugs against this target developed by several companies have entered phase III or II clinical trials, respectively. The indications of these antibodies are osteoporosis, bone damage/related osteopathy, and so on. Related patents include: WO2008133722, WO2010130830, WO2013063095, WO2014006100, WO2014081955, WO2005014650, WO2006119062, and WO2008115732. It is worth mentioning that some studies have shown that anti-sclerostin antibodies are not in conflict with treatment using traditional bisphosphonates, and these two drugs may be used in combination.

The present invention provides novel antibodies developed against a new target for the treatment of bone diseases such as osteoporosis, the antibody being characterized by high affinity, high efficacy, extended half-life and a reduced number of administrations. In addition, the novel molecules of the present invention have high solubility and good stability, which makes it easier to produce a preparation, thereby reducing production costs.

SUMMARY OF THE INVENTION

The antibodies of the present invention are chimeric monoclonal antibodies or humanized monoclonal antibodies, comprising a specific polypeptide sequence disclosed herein, which specifically binds to human sclerostin with high affinity and can be used to increase at least one selected from the group consisting of bone mass, bone mineral density, bone mineral content and bone strength of a mammal, preferably of a human.

The present invention provides a SOST antibody or antigen-binding fragment thereof, comprising at least one CDR region, wherein the CDR region is selected from the following sequences or a mutant thereof, or amino acid sequences having at least 95% identity to the following:

heavy chain variable region HCDR sequence: SEQ ID NO: 7, SEQ ID NO:8 or SEQ ID NO:9;
and
light chain variable region LCDR sequence: SEQ ID NO: 10, SEQ ID NO: 11 or SEQ ID NO: 12.

In a preferred embodiment of the present invention, provided herein is a SOST antibody or antigen binding fragment thereof as described above, wherein the antibody heavy chain variable region comprises at least one HCDR region selected from the following sequences or a mutant thereof: SEQ ID NO: 7, SEQ ID NO: 8 and SEQ ID NO: 9.

In a preferred embodiment of the present invention, provided herein is a SOST antibody or antigen binding fragment thereof as described above, wherein the antibody light chain variable region comprises at least one LCDR region selected from the following sequences or a mutant thereof: SEQ ID NO: 10, SEQ ID NO: 11 and SEQ ID NO: 12.

In a preferred embodiment of the present invention, provided herein is a SOST antibody or antigen binding fragment thereof as described above, wherein the antibody comprises HCDR region sequences SEQ ID NO: 7 (HCDR1), SEQ ID NO: 8 (HCDR2) and SEQ ID NO: 9 (HCDR3), or a mutant thereof, and LCDR region sequences SEQ ID NO: 10 (LCDR1), SEQ ID NO: 11 (LCDR2) and SEQ ID NO: 12 (LCDR3), or a mutant thereof.

In a preferred embodiment of the present invention, provided herein is a SOST antibody or antigen binding fragment thereof as described above, wherein the mutant of the CDR region is a CDR region which has 1-3 amino acid mutation(s) that optimize(s) antibody activity, wherein the mutant of the HCDR2 region preferably is shown in SEQ ID NO: 13.

In a preferred embodiment of the present invention, provided herein is a SOST antibody or antigen binding fragment thereof as described above, wherein the antibody or the antigen-binding fragment thereof is a murine antibody or fragment thereof.

In a preferred embodiment of the present invention, provided herein is a SOST antibody or antigen binding fragment thereof as described above, wherein the heavy chain variable region sequence of the murine antibody is shown in SEQ ID NO: 5, or amino acid sequences having at least 95% identity to SEQ ID NO: 5.

In a preferred embodiment of the present invention, provided herein is a SOST antibody or antigen binding fragment thereof as described above, wherein the light chain variable region sequence of the murine antibody is shown in SEQ ID NO: 6, or amino acid sequences having at least 95% identity to SEQ ID NO: 6.

In a preferred embodiment of the present invention, provided herein is a SOST antibody or antigen binding fragment thereof as described above, wherein the heavy chain variable region sequence of the murine antibody is shown in SEQ ID NO: 5, and the light chain variable region sequence of the murine antibody is shown in SEQ ID NO: 6.

In a preferred embodiment of the present invention, provided herein is a murine antibody or fragment thereof as described above, wherein the antibody heavy chain variable region further comprises a heavy chain FR region derived from murine IgG1, IgG2, IgG3 or IgG4, or a variant thereof.

In a preferred embodiment of the present invention, provided herein is a murine antibody or fragment thereof as described above which further comprises a heavy chain constant region derived from murine IgG1, IgG2, IgG3 or IgG4, or a variant thereof.

In a preferred embodiment of the present invention, provided herein is a murine antibody or fragment thereof as described above, wherein the antibody light chain variable region further comprises a light chain FR region selected from a murine and λ chain, or a variant thereof.

In a preferred embodiment of the present invention, provided herein is a murine antibody or fragment thereof as described above, which further comprises a light chain constant region selected from a murine κ and λ chain, or a variant thereof.

In a preferred embodiment of the present invention, provided herein is a SOST antibody or antigen-binding fragment thereof as described above, wherein the antibody is a chimeric antibody or humanized antibody or the fragment thereof.

In a preferred embodiment of the present invention, provided herein is a humanized SOST antibody or fragment thereof as described above, wherein the heavy chain variable region of the humanized antibody further comprises a heavy chain FR region derived from human IgG1, IgG2, IgG3 or IgG4, or a variant thereof.

In a preferred embodiment of the present invention, provided herein is a humanized SOST antibody or fragment thereof as described above, wherein the heavy chain FR region sequence of the humanized antibody heavy chain variable region is derived from the framework sequence of the FR1, FR2, FR3 region and FR4 region of the human germline heavy chain IGHV1-18*01, or a mutant thereof, preferably the mutant sequence comprises 0-10 amino acid back-mutation(s).

In a preferred embodiment of the present invention, provided herein is a humanized SOST antibody or fragment thereof as described above, wherein the humanized antibody comprises a heavy chain variable region sequence selected from SEQ ID NOs: 14-16, or a mutant thereof and amino acid sequences having at least 95% identity to SEQ ID NOs: 14-16.

In a preferred embodiment of the present invention, provided herein is a humanized SOST antibody or fragment thereof as described above, wherein the light chain FR region sequence on the humanized antibody light chain variable region is derived from the framework sequence of the FR1, FR2, FR3, and FR4 region of the human germline light chain IGKV1-39*01 and/or IGKV4-1*01 or a mutant thereof, preferably the mutant comprises 0-10 amino acid back-mutation(s).

In a preferred embodiment of the present invention, provided herein is a humanized SOST antibody or fragment thereof as described above, wherein the humanized antibody comprises a light chain variable region sequence selected from SEQ ID NOs: 17-19 or a mutant thereof and amino acid sequences having at least 95% identity to SEQ ID NOs: 17-19.

In a preferred embodiment of the present invention, provided herein is a humanized SOST antibody or fragment thereof as described above, wherein the humanized antibody comprises a heavy chain variable region selected from SEQ ID NOs: 14-16 and a light chain variable region selected from SEQ ID NOs: 17-19.

In a preferred embodiment of the present invention, provided herein is a humanized SOST antibody or fragment thereof as described above, wherein the humanized antibody comprises a combination of a heavy chain variable region sequence and a light chain variable region sequence selected from any one of (a) to (c):

(a) Heavy chain variable region sequence of SEQ ID NO: 14, and light chain variable region sequence of SEQ ID NO: 17;

(b) Heavy chain variable region sequence of SEQ ID NO: 15, and light chain variable region sequence of SEQ ID NO: 18; and (c) Heavy chain variable region sequence of SEQ ID NO: 16, and light chain variable region sequence of SEQ ID NO: 19.

In a preferred embodiment of the present invention, provided herein is a humanized SOST antibody or fragment thereof as described above, wherein the heavy chain constant region of the humanized antibody comprises a constant region derived from human IgG1 or a variant thereof, human IgG2 or a variant thereof, human IgG3 or a variant thereof, or human IgG4 or a variant thereof, preferably a constant region derived from human IgG1 or a variant thereof or human IgG4 or a variant thereof, most preferably a constant region derived from IgG4 or a variant thereof. The constant region can also involve some modifications, such as "YTE" to change performance.

In a preferred embodiment of the present invention, provided herein is a humanized SOST antibody or fragment thereof as described above, wherein the humanized antibody comprises a full-length heavy chain sequence selected from SEQ ID NOs: 24-26 or sequences having at least 90% identity to SEQ ID NOs: 24-26.

In a preferred embodiment of the present invention, provided herein is a humanized SOST antibody or fragment thereof as described above, wherein the light chain variable region of the humanized antibody further comprises a light chain FR region optionally selected from human κ and λ chain, or a variant thereof.

In a preferred embodiment of the present invention, provided herein is a humanized SOST antibody or fragment thereof as described above, which further comprises a light chain constant region selected from human κ and λ, or a variant thereof.

In a preferred embodiment of the present invention, provided herein is a humanized SOST antibody or fragment thereof as described above, wherein the humanized antibody comprises a full-length light chain sequence selected from SEQ ID NOs: 27-29 and sequences having at least 90% identity to SEQ ID NOs: 27-29.

In a preferred embodiment of the present invention, provided herein is a humanized SOST antibody or fragment thereof as described above, wherein the humanized antibody comprises a full-length heavy chain selected from SEQ ID NOs: 24-26 and a full-length light chain selected from SEQ ID NOs: 27-29.

In a preferred embodiment of the present invention, provided herein is a humanized SOST antibody or fragment thereof as described above, wherein the humanized antibody comprises a combination of a full-length light chain sequence and a full-length heavy chain sequence selected from any one of the following:

Ab-10: The heavy chain shown as SEQ ID NO: 24 and the light chain shown as SEQ ID NO: 27;

Ab-9: The heavy chain shown as SEQ ID NO: 25 and the light chain shown as SEQ ID NO: 28; and Ab-5: The heavy chain shown as SEQ ID NO: 26 and the light chain shown as SEQ ID NO: 29.

In a preferred embodiment of the present invention, provided herein is a SOST antibody or antigen-binding fragment thereof as described above, wherein the antigen-binding fragment is Fab, Fv, sFv or F(ab')$_2$.

The present invention further provides a DNA sequence encoding an expression precursor product of the SOST antibody or the antigen-binding fragment thereof described above.

The present invention further provides an expression vector comprising the DNA sequence as described above.

The present invention further provides a host cell transformed with the expression vector as described above.

In a preferred embodiment of the present invention, provided herein is a host cell as described above, wherein the host cell is a mammalian cell, preferably CHO cells.

The present invention further provides a pharmaceutical composition, which comprises the SOST antibody or antigen-binding fragment thereof as described above, and one or more pharmaceutically acceptable excipients, diluents or carriers.

The present invention further provides use of the SOST antibody or antigen-binding fragment thereof as described above, or the pharmaceutical composition containing the same, in the preparation of a medicament for enhancing at least one of bone mass, bone mineral density, bone mineral content and bone strength.

The present invention further provides use of the SOST antibody or antigen-binding fragment thereof as described above, or the pharmaceutical composition containing the same, in the preparation of a medicament for treating an SOST-mediated bone disease or disorder, wherein the disease or disorder is selected from the group consisting of osteoporosis, osteopenia or osteoarthritis, rheumatoid arthritis, periodontal disease, and multiple myeloma disease or disorder, preferably osteoporosis.

The present invention further provides a method for treating or preventing an SOST-mediated disease or disorder, comprising administering to a subject in need thereof a therapeutically effective amount of the SOST antibody or the antigen-binding fragment thereof as described above, or the pharmaceutical composition comprising the same, wherein the disease or disorder is selected from the group consisting of osteoporosis, osteopenia or osteoarthritis, rheumatoid arthritis, periodontal disease, and multiple myeloma disease or disorder, preferably osteoporosis.

DETAILED DESCRIPTION OF THE INVENTION

Figure 1:
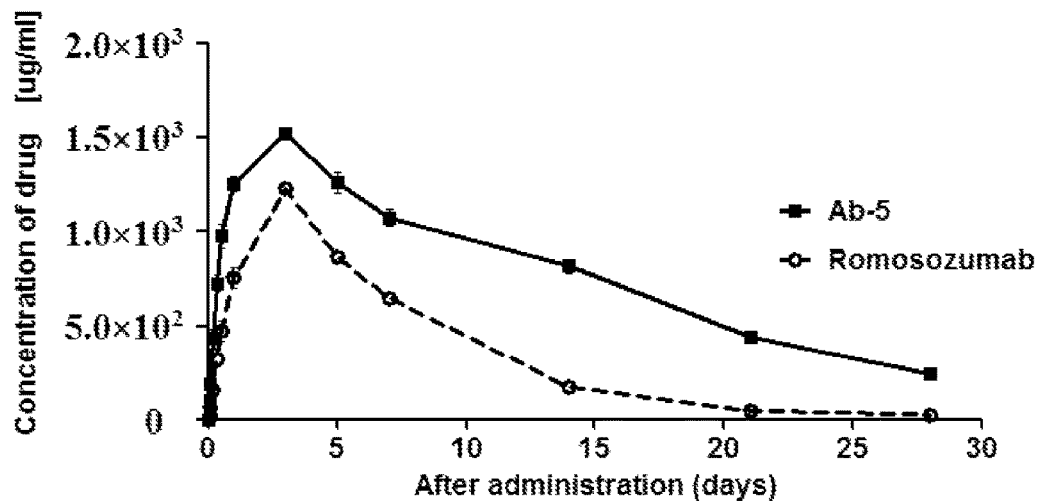
FIG. 1 shows the drug concentration-time curve of the humanized anti-SOST antibody of the present invention in cynomolgus monkey. The results show that, at the same dose, the $AUC_{0-t}$ (mg/ml*day) obtained by using the humanized antibody of the present invention was 22.3, which was more than 2 times as much as that of the positive antibody Romosozumab (9.95)

It is well known to those skilled in the art that the dosage of a drug depends on a variety of factors including, but not limited to the following: the activity of the specific compounds used, the patient's age, the weight of the patient, the patient's health condition, the patient's diet, the time of administration, the mode of administration, the rate of excretion, the combination of drugs, etc. In addition, the optimal treatment modalities, such as the mode of treatment, the daily dosage of the antibody or its composition, or the type of pharmaceutically acceptable salt, can be validated according to traditional treatment regimens.

In order to make the invention more easily understood, certain technical and scientific terms are specifically defined below. Unless specifically defined elsewhere herein, all other technical and scientific terms used herein have the same meaning as those commonly understood by one of ordinary skilled in the art to which this invention belongs.

Terms

As used herein, the single-letter code and the three-letter code for amino acids are described in *J. Biol. Chem.*, 243, p 3558 (1968).

When used herein, the term "Sclerostin" or "SOST" or "SOST protein" refers to the sclerostin (SOST) gene expression product (protein). Unless otherwise specified, such as the murine SOST (m-SOST) or the cynomolgus monkey SOST (cyno-SOST), this term refers to the human SOST (h-SOST) in the present invention. The nucleotide sequences of human, murine and cynomolgus monkey SOST used in the present invention are obtained from GenBank, for example, NP_079513.1 provides a human SOST protein sequence.

The term "antibody" in reference to an anti-sclerostin antibody of the invention (or simply, "antibody of the invention"), as used herein, refers to a monoclonal antibody. The monoclonal antibody or mAb according to the present invention refers to an antibody obtained from a single clonal cell strain which is not limited to a eukaryotic, prokaryotic or phage cloned cell line. Monoclonal antibodies or antigen-binding fragments thereof can be obtained by recombination, for example, hybridoma techniques, recombinant techniques, phage display techniques, synthesis techniques, or other combinations of prior art or other techniques readily known in the art.

A "monoclonal antibody" or "antibody of the invention" or simply "antibody" can be an intact antibody (comprising an intact or full-length Fc region), or a portion or fragment of an antibody comprising an antigen-binding portion, e.g., a Fab fragment, Fab' fragment, or F(ab')2 fragment of a chimeric or humanized antibody. Particularly preferred antigen-binding fragments of an antibody of the invention retain the ability to inhibit or neutralize one or more bioactivity characteristics of a mammalian sclerostin in vivo or in vitro. For example, in one embodiment, an antigen-binding portion of an antibody of the invention can inhibit the interaction of human sclerostin with one or more of its ligands and/or can inhibit one or more receptor-mediated functions of human sclerostin.

Furthermore, a "monoclonal antibody" or "antibody of the invention" or simply "antibody" as used herein can be a single chain Fv fragment that can be produced by joining DNA encoding the LCVR and HCVR with a linker sequence (See, Pluckthun, *The Pharmacology of Monoclonal Antibodies*, vol. 113, Rosenburg and Moore eds., Springer-Verlag, New York, pp 269-315, 1994). It is understood that regardless of whether antigen-binding fragments or portions are specified, the term "antibody" as used herein includes such fragments or portions as well as single chain forms. Unless indicated otherwise, a protein is included within the term "antibody", as long as the protein retains the ability to specifically bind sclerostin.

The terms "anti-sclerostin antibody", "antibody specific for binding to human sclerostin", "anti-SOST antibody", "anti-SOST", "SOST antibody" and "antibody binding to SOST" in the present invention refer to an antibody that is capable of binding to SOST with sufficient affinity, so that the antibody can be used as a diagnostic agent and/or a therapeutic agent for targeting SOST.

As used herein, the term "specific binding" is determined by techniques available in the art, such as competitive ELISA, BIACORE® assay, or KINEXA® assay. For example, the term is also applicable, when the antigen binding domain of the antibody of the invention is specific for a particular epitope carried by many antigens, in which case, the antibody carrying the antigen binding domain can specifically bind to a variety of antigens carrying such epitope. The term "epitope" refers to a molecular moiety that can be recognized and bound by an antibody in the antigen-binding region of one or more antibodies.

The phrase "bioactivity" in reference to an antibody of the invention, includes, but is not limited to, epitope or antigen binding affinity, ability to neutralize or antagonize a bioactivity of sclerostin in vivo or in vitro, $IC_{50}$ measured in a binding assay of sclerostin antibody in vitro binding to and blocking human sclerostin and LRP-6 (e.g., as described in Examples 1 and 2 herein) or measured in other in vitro activity assays, and the in vivo and/or in vitro stability of the antibody. The aforementioned properties or characteristics can be observed or measured by using art-recognized techniques including, but not limited to, ELISA, competitive ELISA, surface plasmon resonance analysis, in vitro and in vivo neutralization assays without limit, receptor binding and immunohistochemistry with tissue sections from different sources (including human, primate) or any other source as may be needed.

The phrase "bioactivity" in reference to sclerostin, includes, but is not limited to, specific binding of sclerostin to another protein (e.g., a receptor or TGF-β family member), one or more receptor-mediated function(s) of human sclerostin, signal transduction, immunogenic properties, in vivo or in vitro stability, affecting the level or activity of another protein in vivo or in vitro (see e.g., Examples 1-5), and sclerostin expression level and tissue distribution.

The term "inhibit" or "neutralize" as used herein, with respect to a bioactivity of an antibody of the invention, means the ability to substantially antagonize, prohibit, prevent, restrain, slow, disrupt, eliminate, stop, reduce or reverse a bioactivity of sclerostin (e.g., as measured in Example 2 herein).

The term "Kabat numbering" as used herein is recognized in the art and refers to a system of numbering amino acid residues that are more variable (i.e., hypervariable) than other amino acid residues in heavy and light chain regions of an antibody (Kabat, et al., Ann. NY Acad. Sci. 190:382-93 (1971); Kabat, et al., Sequences of Proteins of Immunological Interest, Fifth Edition, U.S. Department of Health and Human Services, NIH Publication No. 91-3242 (1991)). The positioning of CDRs in the variable region of an antibody follows Kabat numbering or simply "Kabat."

The terms "subject" and "patient" used interchangeably herein, refer to a mammal, preferably a human. In a certain embodiment, the subject is further characterized as suffering from a disease, disorder or condition that would benefit from a decreased level of sclerostin or decreased bioactivity of sclerostin.

The term "vector" refers to a nucleic acid molecule capable of transporting another nucleic acid to which it has been operably linked. Such term includes, but is not limited to plasmids and viral vectors. Certain vectors are capable of autonomous replication in a host cell into which they are introduced, while other vectors can be integrated into the genome of a host cell upon introduction into the host cell, and thereby the vectors are replicated along with the host genome. Moreover, certain vectors are capable of directing the expression of genes to which they are operably linked. Such vectors are referred to herein as "recombinant expression vectors" (or simply "expression vectors"). Exemplary vectors are well known in the art.

As used herein, the expressions "cell", "host cell", and "cell culture" are used interchangeably and include any cell or cell culture that is a recipient of any isolated polynucleotide of the invention or any recombinant vector(s) comprising a nucleotide sequence encoding a HCVR, LCVR or antibody of the invention. A host cell includes cells transformed, transduced or infected with one or more recombinant vector(s) or a polynucleotide expressing a monoclonal antibody of the invention or a light chain or heavy chain thereof.

Each heavy chain of a full-length antibody comprises an N-terminal heavy chain variable region (herein "HCVR") and a heavy chain constant region. Each light chain of a full-length antibody comprises an N-terminal light chain variable region (herein "LCVR") and a light chain constant region. The HCVR and LCVR region can be further subdivided into hypervariable regions, termed complementarity determining regions ("CDRs"). Interspersed within CDRs, regions that are more conserved are termed framework regions ("FRs"). The functional ability of an antibody to bind a particular antigen or epitope is largely influenced by the six CDRs present in the variable region of the antibody. Each HCVR and LCVR comprises three CDRs (HCDR1, HCDR2 and HCDR3 in the HCVR and LCDR1, LCDR2 and LCDR3 in the LCVR) and four FRs, arranged from amino-terminus to carboxy-terminus in the following order: FR1, CDR1, FR2, CDR2, FR3, CDR3, FR4. The CDRs contain most of the residues which form specific interactions with the antigen. CDR positioning within the variable region follows Kabat.

Light chains are classified as kappa or lambda, and are characterized by a particular constant region as known in the art. Heavy chains are classified as gamma, mu, alpha, delta, or epsilon, and define the antibody's isotype as IgG, IgM, IgA, IgD, and IgE, respectively. Some of those isotypes in turn may be further divided into subclasses e.g., IgG1, IgG2, IgG3, IgG4. Each heavy chain type is characterized by a particular constant region with a sequence readily known in the art. Light chain constant region kappa and heavy chain constant regions IgG1, IgG2, IgG3, IgG4 are preferred constant regions in the antibodies of the invention. Chimeric antibodies may have constant regions from non-human origin, preferably rat or murine.

As used herein, the "antigen-binding region" or "antigen-binding portion" refers to a portion within the variable region of an antibody molecule, which contains the amino acid residues that interact with an antigen and confer the antibody with specificity and affinity for the antigen. This antibody portion includes the framework amino acid residues necessary for maintaining the proper conformation of the antigen-binding residues.

A preferred antibody of the present invention comprises six CDRs having amino acid sequences of SEQ ID NOs: 7, 8, 9, 10, 11 and 12. A more preferred antibody of the present invention comprises six CDRs having amino acid sequences of SEQ ID NOs: 19, 27, 28, 32, 36 and 40. More preferably, the optimized CDRs in the antibodies of the invention comprise at least one amino acid substitution when compared to the CDRs present in the parent antibody, the optimized CDRs in the antibodies of the invention comprise six CDRs having amino acid sequences of SEQ ID NOs: 7, 13, 9, 10, 11 and 12. The CDRs of these preferred antibodies exist at the position as stated in Table 1 below. The CDRs are positioned in the variable region according to Kabat.

A preferred antibody of the invention comprises a HCVR having the amino acid sequence of SEQ ID NO 14, 15 and 16. Other preferred monoclonal antibodies of the invention comprise a LCVR having the amino acid sequence of SEQ ID NO: 17, 18 and 19. More preferably, an antibody of the invention comprises a LCVR of SEQ ID NO: 17 and a HCVR of SEQ ID NO: 14. An alternative antibody of the invention comprises a LCVR of SEQ ID NO: 18 and a HCVR of SEQ ID NO: 15. A more preferred antibody of the invention comprises a HCVR of SEQ ID NO: 16 and a LCVR of SEQ ID NO: 19. Such HCVRs of the invention are preferably linked to a heavy chain constant region, preferably of human origin, preferably a heavy chain constant region of IgG1 or IgG4, most preferably a heavy chain constant region of IgG4. Such LCVRs are preferably linked to a light chain constant region, preferably of human origin, preferably a kappa chain.

One preferred antibody of the present invention comprises a heavy chain polypeptide having the amino acid sequence of SEQ ID NO: 24 and a light chain polypeptide having the amino acid sequence of SEQ ID NO: 27.

Another preferred antibody of the present invention comprises a heavy chain polypeptide having the amino acid sequence of SEQ ID NO: 25 and a light chain polypeptide having the amino acid sequence of SEQ ID NO: 28.

Another preferred antibody of the present invention comprises a heavy chain polypeptide having the amino acid sequence of SEQ ID NO: 26 and a light chain polypeptide having the amino acid sequence of SEQ ID NO: 29.

The SEQ ID NOs of their sequences are as listed in Table 1 below.

TABLE 1

Sequence listing of mAb variable region

| Antibody | Heavy Chain CDR1 (SEQ ID NO) | Heavy Chain CDR2 (SEQ ID NO) | Heavy Chain CDR3 (SEQ ID NO) | Light Chain CDR1 (SEQ ID NO) | Light Chain CDR2 (SEQ ID NO) | Light Chain CDR3 (SEQ ID NO) |
|---|---|---|---|---|---|---|
| Parent antibody | 7 | 8 | 9 | 10 | 11 | 12 |
| Optimized humanized antibody | 7 | 13 | 9 | 10 | 11 | 12 |

Preferably, an antibody of the present invention is further characterized by having a $K_D$ for human sclerostin of less than about 10 nM, 3 nM, 1 nM or 0.3 nM, more preferably less than about 0.1 nM. Additionally, it is preferred that such antibody is further defined by having a $K_D$ for cynomolgous monkey sclerostin of less than about 10 nM, 3 nM, 1 nM or 0.3 nM, or more preferably less than about 0.1 nM.

Preferably, an antibody of the present invention is further characterized by having an $IC_{50}$ of 100 nM or less, about 50 or 30 nM or less, more preferably about 25 nM, even more preferably about 20 nM (e.g., 17.9 nM) or less, as measured in experiments of blocking the binding between human sclerostin and LRP-6 (see, e.g., Example 2 herein).

More preferably, an antibody of the present invention is further characterized by having a $K_D$ for human sclerostin of less than about 10 nM, 3 nM, 1 nM or 0.3 nM, more preferably less than about 0.1 nM, and is also characterized by having an $IC_{50}$ of 100 nM or less, about 50 or 30 nM or less, more preferably about 25 nM, even more preferably about 20 nM (e.g., 17.9 nM) or less, as measured in experiments of blocking the binding between human sclerostin and LRP-6. The six CDRs, HCVR, LCVR, HCVR and LCVR, the entire heavy chain, the entire light chain, or the entire heavy chain and the entire light chain within said antibody are defined by particular sequence as shown in the SEQ ID NOs herein.

Even more preferably, an antibody of the present invention is further characterized by having a $K_D$ for human sclerostin of less than about 10 nM, 3 nM, 1 nM or 0.3 nM, more preferably less than about 0.1 nM, and is also characterized by having an $IC_{50}$ of 100 nM or less, about 50 or 30 nM or less, more preferably about 25 nM, even more preferably about 20 nM (e.g., 17.9 nM) or less, as measured in experiments of blocking the binding between human sclerostin and LRP-6; and is also characterized by having a $K_D$ of less than 10 nM, 3 nM, 1 nM or 0.3 nM, more preferably less than about 0.1 nM, as measured in in vitro ELISA binding experiments of sclerostin antibody by using cyno sclerostin. The six CDRs, HCVR, LCVR, HCVR and LCVR, the entire heavy chain, the entire light chain, or the entire heavy chain and the entire light chain within said antibody are defined by particular sequences as shown in the SEQ ID NOs herein.

Expression of Antibody

The present invention is also directed to host cells that express an anti-sclerostin antibody of the invention. Establishment and isolation of host cell lines producing an antibody of the invention can be accomplished by using standard techniques known in the art.

A wide variety of host expression systems known in the art can be used to express an antibody of the present invention, including prokaryotic (bacterial) and eukaryotic expression systems (such as yeast, baculovirus, plant, mammalian and other animal cells, transgenic animals, and hybridoma cells), as well as phage display expression systems.

An antibody of the invention can be prepared by recombinant expression of immunoglobulin light and heavy chain genes in a host cell. To express an antibody recombinantly, a host cell is transformed, transduced, or infected with one or more recombinant expression vectors carrying DNA fragments encoding the immunoglobulin light and/or heavy chains of the antibody, such that the light and/or heavy chains are expressed in the host cell. The heavy chain and the light chain may be expressed independently from different promoters to which they are operably linked in one vector or, alternatively, the heavy chain and the light chain may be expressed independently from different promoters to which they are operably linked in two vectors (one expressing the heavy chain and one expressing the light chain). Optionally, the heavy chain and light chain may be expressed in different host cells.

Additionally, the recombinant expression vector can encode a signal peptide that facilitates secretion of the anti-sclerostin antibody light and/or heavy chain from a host cell. The anti-sclerostin antibody light and/or heavy chain gene can be cloned into the vector, such that the signal peptide is operably linked in-frame to the amino terminus of the antibody chain gene. The signal peptide can be an immunoglobulin signal peptide or a heterologous signal peptide. Preferably, the recombinant antibodies are secreted into the medium in which the host cells are cultured, from which the antibodies can be recovered or purified.

An isolated DNA encoding a HCVR region can be converted to a full-length heavy chain gene by operably linking the HCVR-encoding DNA to another DNA molecule encoding the heavy chain constant region. The sequences of heavy chain constant region genes of humans as well as other mammals are known in the art. DNA fragments encompassing these regions can be obtained e.g., by standard PCR amplification. The heavy chain constant region can be of any type, (e.g., IgG, IgA, IgE, IgM or IgD), any class (e.g., IgG1, IgG2, IgG3 or IgG4) or subclass constant region and any allotypic variant thereof as described in Kabat (supra). A preferred heavy chain constant region comprises a constant region of IgG1 or a variant thereof or IgG4 or a variant thereof.

An isolated DNA encoding a LCVR region can be converted to a full-length light chain gene (as well as to a Fab light chain gene) by operably linking the LCVR-encoding DNA to another DNA molecule encoding a light chain constant region. The sequences of light chain constant region genes of humans as well as other mammals are known in the art. DNA fragments encompassing these regions can be obtained by methods such as standard PCR amplification. The light chain constant region can be a kappa or lambda constant region.

Preferred mammalian host cells for use in the invention are CHO cells (e.g., ATCC CRL-9096), HEK 293E cells (e.g. ATCC CRL-1573), NSO cells, SP2/0 cells and COS cells (ATCC e.g., CRL-1650, CRL-1651). Additional host cells for use in the invention include other mammalian cells, yeast cells and prokaryotic cells. When recombinant expression vectors encoding antibody genes are introduced into mammalian host cells, the antibodies are produced by culturing the host cells for a period of time sufficient to allow for expression of the antibody in the host cells or, more preferably, for a period of time sufficient to allow for secretion of the antibody into the culture medium in which the host cells are grown. Antibodies can be recovered from the host cell and/or the culture medium using standard purification methods.

The expressed product (in the form of whole antibody, light chain and heavy chain or other forms of immunoglobulin) can be purified according to standard procedures in the art, including ammonium sulfate precipitation; ion exchange, affinity, reverse phase, and hydrophobic interaction column chromatography; gel electrophoresis and the like. Substantially pure immunoglobulins of at least about 90%, 92%, 94% or 96% homogeneity are preferred, and 98 to 99% or higher homogeneity is most preferred, for pharmaceutical uses. Once purified, partially purified or purified to a desired homogeneity, the sterile antibodies can then be used therapeutically, as directed herein.

Humanized Antibody

Preferably, an antibody of the invention to be used for therapeutic purpose, has the sequence of the framework and constant region (to the extent it exists in the antibody) derived from the mammal in which the antibody will be used as a therapeutic agent to decrease the possibility that the therapeutic antibody will induce and immune response against the therapeutic antibody in the mammal. Humanized antibodies are of particular interest, since they are valuable for therapeutic application and decrease the likelihood of a human anti-mouse antibody response, which is frequently observed when antibodies of murine origin or antibodies comprising portions of murine origin are administered to a human subject. Preferably, injected humanized antibodies may have a half-life more like that of naturally occurring human antibodies when compared with e.g., murine antibodies, thereby allowing less frequent administration or lower doses to be administered to a subject.

The term "humanized antibody" as used herein refers to an antibody wherein at least one portion is of human origin. For example, the humanized antibody can comprise portions derived from an antibody of nonhuman origin (such as a mouse) and portions derived from an antibody of human origin, joined together, e.g., chemically by conventional techniques (e.g., synthesis) or prepared as a contiguous polypeptide using genetic engineering techniques.

Preferably, a "humanized antibody" has CDRs that originate from or are derived from a parent antibody (i.e., a non-human antibody, preferably a mouse monoclonal antibody), while framework and constant regions, to the extent hey are present, (or a significant or substantial portion thereof, i.e., at least about 90%, 92%, 94%, 95%, 96%, 97%, 98% or 99%) are encoded by nucleic acid sequence information that occurs in the human germline immunoglobulin region (see, e.g., the International ImMunoGeneTics Database) or in recombined or mutated forms thereof, regardless of whether or not said antibodies are produced in a human cell. Preferably, at least two, three, four, five or six CDRs of a humanized antibody are optimized from CDRs of a non-human parent antibody from which the humanized antibody was derived, to generate a desired property, e.g., improved specificity, affinity or neutralization, which can be identified by a screening assay, e.g., an ELISA assay. Preferably, an optimized CDR in an antibody of the invention comprises at least one amino acid substitution when compared to that present in the parent antibody. Certain amino acid substitutions in the CDRs of humanized antibodies of the invention, when compared with those of parent antibodies (see Example 4 herein), decrease the likelihood of instability of the antibody (e.g., removal of Asn residues in the CDR) or decrease immunogenicity of the antibody when administered to a human subject (e.g., as predicted by IMMUNOFILTER™ Technology).

Humanized antibodies preferably contain minimal sequence derived from a non-human antibody. Humanized antibodies can comprise residues that are found neither in the recipient antibody nor in the CDR or framework sequences imported from the parent antibody. Humanized antibodies can be subjected to in vitro mutagenesis using routine methods in the art and, thus, the framework region amino acid sequences of the HCVR and LCVR regions of the humanized recombinant antibodies are sequences that, while derived from those related to human germline HCVR and LCVR sequences, may not naturally exist within the human antibody germline repertoire in vivo. It is contemplated that such amino acid sequences of the HCVR and LCVR framework regions of the humanized recombinant antibodies are at least 90%, 92%, 94%, 95%, 96%, 98% or more preferably at least 99% or most preferably 100% identical to a human germline sequence.

In a preferred embodiment, the humanized antibody of the invention comprises a human germline heavy chain framework sequence and a human germline light chain framework sequence. Such framework sequences can be obtained from public DNA databases covering germline antibody gene sequences or from published references. For example, germline DNA sequences of human heavy and light chain variable region genes can be found in "VBase" human germline sequence database (available on the web www.m-rccpe.com.ac.uk/vbase), as well as found in Kabat, E A, et al 1991 Sequences of Proteins of Immunological Interest, 5th Ed. In a preferred embodiment of the invention, wherein the murine CDR sequences of a SOST humanized antibody are selected from SEQ ID NOs: 7, 8, 9, 10, 11 and 12, human antibody variable region frameworks were designed and selected, wherein the light chain FR region sequences on the light chain variable region of the antibody are derived from FR1, FR2, FR3, and FR4 regions of the human germline light chain IGKV1-39*01 and IGKV4-1*01; and the heavy chain FR region sequences on the heavy chain variable region of the antibody are derived from FR1, FR2, FR3, and FR4 regions of the human germline heavy chain IGHV1-18*01.

There are multiple methods available in the art to generate humanized antibodies. For example, humanized antibodies can be produced by obtaining nucleic acid sequences encoding the HCVR and LCVR of a parent antibody (e.g., a murine antibody or antibody made by a hybridoma), which specifically binds sclerostin, preferably human sclerostin, identifying the CDRs in said HCVR and LCVR (nonhuman), and grafting such CDR-encoding nucleic acid sequences onto selected human framework-encoding nucleic acid sequences. Optionally, a CDR region can be optimized by random mutagenesis or at particular locations in order to substitute one or more amino acids in the CDR with a different amino acid prior to grafting the CDR region into the framework region. Alternatively, a CDR region can be optimized subsequent to insertion into the human framework region using methods available to one skilled in the art.

After the CDR-encoding sequences are grafted onto the selected human framework encoding sequences, the resultant DNA sequences encoding the humanized variable heavy and variable light chain sequences are then expressed to produce a humanized antibody that binds sclerostin. The humanized HCVR and LCVR can be expressed as part of a whole anti-sclerostin antibody molecule, i.e., as a fusion protein with human constant domain sequences. However, the HCVR and LCVR sequences can also be expressed to produce a humanized anti-sclerostin Fv, in the absence of constant sequences.

References further describing methods which involve the humanization of a mouse antibody that may be used, include e.g., Queen et al., *Proc. Natl. Acad. Sci. USA* 88:2869, 1991 and the method of Winter and co-workers (Jones et al., *Nature,* 321:522 (1986); Riechmann et al., *Nature,* 332:323-327 (1988); Verhoeyen et al., *Science,* 239:1534 (1988)).

Therapeutic Uses

A pharmaceutical composition comprising an anti-sclerostin monoclonal antibody of the invention can be used to increase at least one of bone mass, bone mineral density, bone mineral content and bone strength in either vertebral or non-vertebral bone, or both, when an effective amount is administered to a human subject in need thereof. A pharmaceutical composition comprising an anti-sclerostin monoclonal antibody of the invention can be used to reduce the incidence of fracture of vertebral and/or non-vertebral bone, when an effective amount is administered to a human subject in need thereof. Reducing the incidence of fracture includes reducing the likelihood or actual incidence of fracture for a human subject when compared with an untreated control population.

Furthermore, an antibody of the invention can be useful for the treatment of conditions, diseases, or disorders, wherein the presence of sclerostin causes or contributes to undesirable pathological effects; or a decrease of sclerostin levels or sclerostin bioactivity has a therapeutic benefit in human subjects. Such conditions, diseases, or disorders include, but are not limited to, osteoporosis, osteopenia, osteoarthritis, pain associated with osteoarthritis, periodontal disease, and multiple myeloma. Subjects can be male or female. Preferably, a human subject is at risk of fracture of vertebral and/or non-vertebral bone, more preferably a human subject is at risk of, or suffering from, osteoporosis. The human subject is preferably a female and more preferably a female at risk of or having post-menopausal osteoporosis. It is contemplated that a subject at any stage of osteoporosis can benefit from the method of the invention.

Additionally, the use of an antibody of the invention in the manufacture of a medicament for the treatment of at least one of the aforementioned disorders is contemplated.

The terms "treatment" and "treating" are intended to refer to all processes, wherein there may be a slowing, interruption, arrest, control, or stopping of the progression of the disorders described herein, but does not necessarily indicate a total elimination of all disorder symptoms. "Treatment", as used herein, includes administration of a compound of the present invention for treatment of a disease or condition in a mammal, particularly in a human, and includes: (a) inhibiting further progression of the disease, i.e., arresting its development; and (b) relieving the disease, i.e., causing regression of the disease or disorder or alleviating symptoms or complications thereof. Dosage regimens can be adjusted to provide the optimum desired response (e.g., a therapeutic response). For example, a single bolus can be administered, several divided doses can be independently administered over time, or the dose can be proportionally reduced or increased as indicated by the exigencies of the therapeutic situation.

Pharmaceutical Composition

An antibody of the invention can be incorporated into a pharmaceutical composition suitable for administration to a human subject. An antibody of the invention can be administered to a human subject alone or in combination with a pharmaceutically acceptable carrier and/or diluent in a single or multiple doses. Such pharmaceutical compositions are designed to be appropriate for the selected mode of administration, and pharmaceutically acceptable diluents, carrier, and/or excipients, such as dispersing agents, buffers, surfactants, preservatives, solubilizing agents, isotonicity agents, stabilizing agents and the like are used as appropriate. Said compositions can be designed in accordance with conventional techniques disclosed in, e.g., Remington, The Science and Practice of Pharmacy, 19th Edition, Gennaro, Ed., Mack Publishing Co., Easton, Pa. 1995 which provides a compendium of formulation techniques as are generally known to practitioners. Suitable carriers for pharmaceutical compositions include any material which, when combined with a monoclonal antibody of the invention, retains the molecule's activity and is non-reactive with the subject's immune system.

A pharmaceutical composition comprising an anti-sclerostin monoclonal antibody of the present invention can be administered to a subject at risk of or exhibiting pathologies as described herein, e.g., osteoporosis, osteoarthritis or other bone degenerative disorders, using standard administration techniques.

A pharmaceutical composition of the invention preferably contains an "effective amount" of an antibody of the invention. An effective amount refers to an amount necessary (at dosages and for periods of time and for the means of administration) to achieve the desired therapeutic result. An effective amount of the antibody can vary according to factors such as the disease state, age, sex, and weight of the individual, and the ability of the antibody or antibody portion to elicit a desired response in the individual. An effective amount is also an amount in which any toxic or detrimental effect of the antibody is outweighed by the therapeutically beneficial effects.

An effective amount is at least the minimal dose, but less than a toxic dose, of an active agent, which is necessary to impart therapeutic benefit to a subject. In other words, an effective amount or therapeutically effective amount of an antibody of the invention is an amount which in mammals, preferably humans, (i) increases at least one of bone mass, bone mineral density, bone mineral content and bone strength, or (ii) treats a condition, disorder or disease, wherein the presence of sclerostin causes or contributes to an undesirable pathological effect, or (iii) a decrease in sclerostin level or sclerostin bioactivity results in a beneficial therapeutic effect in a mammal, preferably a human; wherein the condition, disorder or disease includes, but is not limited to osteoporosis, osteopenia, osteoarthritis, rheumatoid arthritis, periodontal disease, and multiple myeloma.

Hereinafter, the present invention is further described with reference to examples. However, the scope of the present invention is not limited thereto.

In the examples or test examples of the present invention, where specific conditions are not described, the experiments are generally conducted under conventional conditions or in accordance with the conditions suggested by the manufacturer of the raw material or the product. See Sambrook et al., Molecular Cloning, Laboratory Manual, Cold Spring Harbor Laboratory; Contemporary Molecular Biology Approach, written by Ausubel et al., Greene Publishing Association, Wiley Interscience, NY. Where the source of the reagents is not specifically given, the reagents are commercially available conventional reagents.

EXAMPLE

Example 1. SOST Cloning and Expression

The coding sequence of human sclerostin with a His tag (His-h-SOST), the coding sequence of human sclerostin with a Flag tag (h-SOST-Flag), the coding sequence of mouse sclerostin with a Flag tag (m-SOST-Flag), and the coding sequence of cynomolgus monkey sclerostin with a Flag tag (cyno-SOST-Flag) were synthesized by CRO Shanghai Xuguan Biotechnology Development Co., Ltd (The template sequences of the above sclerostin recombinant proteins were designed by the present invention), and cloned into pTT5 vector (Biovector, Cat #: 102762), respectively. The recombinant SOST protein was expressed in 293T cells and purified as described in Example 2. The purified protein was used in the following experiments of the examples.

```
DNA sequence of His-h-SOST:
                                      (SEQ ID NO: 1)
ATGGACATGAGGGTGCCTGCCCAACTGCTGGGCCTGTTGTTGCTTTGGTT

CCCCGGAAGCAGGTGCCATCATCACCACCATCATCAGGGCTGGCAGGCCT

TCAAGAACGACGCAACCGAGATTATCCCCGAACTGGGCGAATATCCCGAG

CCCCCTCCAGAGCTGGAGAATAACAAGACCATGAACAGGGCCGAGAACGG

CGGCAGACCCCCCCATCATCCCTTCGAGACTAAAGACGTGAGCGAGTACA

GCTGCAGGGAGCTGCATTTCACCAGGTACGTGACCGATGGCCCCTGTAGG

AGCGCCAAGCCCGTGACTGAACTGGTGTGCAGCGGCCAGTGCGGTCCGGC

CAGACTGCTGCCGAACGCTATCGGCAGGGGCAAGTGGTGGAGGCCCTCTG
```

-continued

GACCCGACTTCAGGTGCATACCCGACAGGTACCGCGCTCAGAGAGTGCAA

CTGTTGTGTCCTGGGGGCGAGGCTCCGAGGGCGCGAAAGGTGAGGCTGGT

GGCCAGTTGTAAGTGCAAGAGGCTGACCAGGTTCCACAACCAGAGCGAGC

TGAAGGACTTCGGCACCGAAGCAGCCAGGCCGCAGAAGGGCAGGAAGCCC

AGGCCACGAGCACGATCCGCCAAAGCCAATCAGGCAGAGCTCGAGAATGC

CTACTGA

DNA sequence of h-SOST-Flag:
(SEQ ID NO: 2)
ATGGACATGAGGGTGCCTGCCCAACTGCTGGGCCTGTTGTTGCTTTGGTT

CCCCGGAAGCAGGTGCCAGGGCTGGCAGGCCTTCAAGAACGACGCAACCG

AGATTATCCCCGAACTGGGCGAATATCCCGAGCCCCCTCCAGAGCTGGAG

AATAACAAGACCATGAACAGGGCCGAGAACGGCGGCAGACCCCCCCATCA

TCCCTTCGAGACTAAAGACGTGAGCGAGTACAGCTGCAGGGAGCTGCATT

TCACCAGGTACGTGACCGATGGCCCCTGTAGGAGCGCCAAGCCCGTGACT

GAACTGGTGTGCAGCGGCCAGTGCGGTCCGGCCAGACTGCTGCCGAACGC

TATCGGCAGGGGCAAGTGGTGGAGGCCCTCTGGACCCGACTTCAGGTGCA

TACCCGACAGGTACCGCGCTCAGAGAGTGCAACTGTTGTGTCCTGGGGGC

GAGGCTCCGAGGGCGCGAAAGGTGAGGCTGGTGGCCAGTTGTAAGTGCAA

GAGGCTGACCAGGTTCCACAACCAGAGCGAGCTGAAGGACTTCGGCACCG

AAGCAGCCAGGCCGCAGAAGGGCAGGAAGCCCAGGCCACGAGCACGATCC

GCCAAAGCCAATCAGGCAGAGCTCGAGAATGCCTACGACTACAAGGATGA

CGACGACAAGTGA

DNA sequence of m-SOST-Flag:
(SEQ ID NO: 3)
ATGGACATGAGGGTGCCTGCCCAACTGCTGGGCCTGTTGTTGCTTTGGTT

CCCCGGAAGCAGGTGCCAGGGCTGGCAGGCCTTCAGGAACGACGCAACCG

AGGTGATCCCCGGACTGGGCGAATATCCCGAGCCCCCTCCAGAGAATAAC

CAGACCATGAACAGGGCCGAGAACGGCGGCAGACCCCCCCATCATCCCTA

CGACGCTAAAGGCGTGAGCGAGTACAGCTGCAGGGAGCTGCATTACCACA

GGTTCCTGACCGATGGCCCCTGTAGGAGCGCCAAGCCCGTGACTGAACTG

GTGTGCAGCGGCCAGTGCGGTCCGGCCAGACTGCTGCCGAACGCTATCGG

CAGGGTCAAGTGGTGGAGGCCCAACGGACCCGACTTCAGGTGCATACCCG

ACAGGTACCGCGCTCAGAGAGTGCAACTGTTGTGTCCTGGGGCGCCGCT

CCGAGGAGCCGAAAGGTGAGGCTGGTGGCCAGTTGTAAGTGCAAGAGGCT

GACCAGGTTCCACAACCAGAGCGAGCTGAAGGACTTCGGCCCCGAAACAG

CCAGGCCGCAGAAGGGCAGGAAGCCCAGGCCAGGAGCACGAGGAGCCAAA

GCCAATCAGGCAGAGCTCGAGAATGCCTACGACTACAAGGATGACGACGA

CAAGTGA

DNA sequence of cyno-SOST-Flag:
(SEQ ID NO: 4)
ATGGACATGAGGGTGCCTGCCCAACTGCTGGGCCTGTTGTTGCTTTGGTT

CCCCGGAAGCAGGTGCCAGGGCTGGCAGGCCTTCAAGAACGACGCAACCG

AGATTATCCCCGAACTGGGCGAATATCCCGAGCCCCCTCCAGAGCTGGAG

-continued

AATAACAAGACCATGAACAGGGCCGAGAACGGCGGCAGACCCCCCCATCA

TCCCTTCGAGACTAAAGACGTGAGCGAGTACAGCTGCAGGGAGCTGCATT

TCACCAGGTACGTGACCGATGGCCAGTGTAGGAGCGCCAAGCCCGTGACT

GAACTGGTGTGCAGCGGCCAGTGCGGTCCGGCCAGACTGCTGCCGAACGC

TATCGGCAGGGGCAAGTGGTGGAGGCCCTCTGGACCCGACTTCAGGTGCA

TACCCGACAGGTACCGCGCTCAGAGAGTGCAACTGTTGTGTCCTGGGGC

GCCGCTCCGAGGGCGCGAAAGGTGAGGCTGGTGGCCAGTTGTAAGTGCAA

GAGGCTGACCAGGTTCCACAACCAGAGCGAGCTGAAGGACTTCGGCCCCG

AAGCAGCCAGGCCGCAGAAGGGCAGGAAGCCCAGGCCACGAGCACGAGGA

GCCAAAGCCAATCAGGCAGAGCTCGAGAATGCCTACGACTACAAGGATGA

CGACGACAAGTGA

Example 2. Purification of SOST Recombinant Protein

1. Purification Steps of SOST Recombinant Protein with a His Tag

The supernatant from cell expression was centrifuged at high speed to remove impurities, the buffer was exchanged to PBS, and imidazole was added to a final concentration of 5 mM. The nickel column was equilibrated with PBS solution containing 5 mM imidazole and washed with 2-5 column volumes. Subsequently, the supernatant was loaded onto the column. The column was washed with PBS solution containing 5 mM imidazole until the $A_{280}$ reading was reduced to baseline. Then, the chromatography column was washed with PBS plus 10 mM imidazole to remove non-specifically bound proteins, and the effluent was collected. The target protein was eluted with PBS solution containing 300 mM imidazole, and the elution peak was collected.

The collected effluent was further purified by ion exchange (SP column). Solution A was prepared: 0.01M PB, pH 8.0; and solution B was prepared: solution A+1M NaCl. The target protein, which was eluted by PBS solution containing imidazole, was first dialyzed against the solution A, and the SP column was equilibrated with solution A. The sample was loaded; the concentration gradient of B solution was 0-100%; and the target protein was eluted with 10 column volumes and the elution peak was collected. The obtained protein was identified by electrophoresis, peptide mapping and LC-MS, and the correct sample was aliquoted for use. The human sclerostin with a His tag (His-h-SOST) was obtained.

2. Purification Steps of SOST Recombinant Protein with a Flag Tag

The sample was centrifuged at high speed to remove impurities and concentrated to an appropriate volume. The flag affinity column was equilibrated with 0.5×PBS and washed with 2-5 column volumes. The supernatant samples were then loaded onto the column after removing impurities. The column was washed with 0.5×PBS until the $A_{280}$ reading was reduced to baseline. Then, the column was washed with PBS containing 0.3 M NaCl, and the impurity proteins were washed and collected. The target protein was eluted with 0.1 M acetic acid (pH 3.5-4.0) and collected, and the pH was adjusted to neutral. The collected sample was identified by electrophoresis, peptide mapping, LC-MS, and the correct sample was aliquoted for use.

The human sclerostin with a Flag tag (h-SOST-Flag), mouse sclerostin with a Flag tag (m-SOST-Flag) and the cynomolgus monkey sclerostin with a Flag tag (cyno-SOST-Flag) were obtained and used for performance tests of the antibodies of present invention.

Example 3. Production of Monoclonal Antibody Anti-Human SOST

The anti-human SOST monoclonal antibody was produced by immunizing mice. Experimental SJL white mice, female, 6-weeks old (Beijing Weitong Lihua Experimental Animal Technology Co., Ltd., animal production license number: SCXK (Beijing) 2012-0001) were used.

Feeding environment: SPF level. After the mice were purchased, the animals were kept in the laboratory for 1 week, with 12/12 hours light/dark cycle, at a temperature of 20-25° C., and humidity of 40-60%. The mice that had been acclimated to the environment were divided into two groups (A/B), with 10 mice in each group.

Human SOST recombinant protein with a His tag (His-h-tag) was used as an immunogen. In group A, Freund's adjuvant (Sigma Lot Num: F5881/F5506) was used for emulsification. The first immunization was performed with Freund's complete adjuvant (CFA), and the booster immunizations were performed with Freund's incomplete adjuvant (IFA). The ratio of antigen to adjuvant was 1:1, 200 μl/200 μg/mouse (first immunization), and 200 μl/100 μg/mouse (boost). In group B, cross-immunization was performed with Titermax (Sigma Lot Num: T2684) and Alum (Thermo Lot Num: 77161). The ratio of antigen to adjuvant (titermax) was 1:1, and the ratio of antigen to adjuvant (Alum) was 3:1, 200 μl/200 μg/mouse (first immunization), and 200 μl/100 μg/mouse (boost). The antigen was emulsified and inoculated on days 0, 14, 28, 42, 56.

On day 0, the mice in A/B group were intraperitoneally (IP) injected with 50 μg/mouse of the emulsified antigen. On day 14, the mice were subcutaneously (s.c.) injected with 25 μg/mouse at multiple sites (usually 6-8 sites on the back). On days 28 and 42, either back or intraperitoneal injection of the antigen was selected according to the lumps on the back and the swelling conditions in the abdomen. A booster immunization was performed by intraperitoneal (IP) injection of antigen solution formulated with saline at 200 μg/mouse 3 days prior to splenocyte fusion.

A blood titer test was performed on days 22, 36, 50, and 64, and the binding activity of mouse serum to human sclerostin was measured by the ELISA method of Test Example 1, and the results are shown in Table 2. After the fourth immunization, mice with high blood titer tending to platform were selected for splenocyte fusion. Hybridoma cells were obtained by fusing splenocyte with myeloma Sp2/0 cells (ATCC® CRL-8287™) by using an optimized PEG-mediated fusion procedure. The activity of blocking the binding between human SOST and LRP-6 by anti-human SOST antibody in mouse serum was detected according to Test Example 2, and the monoclonal hybridoma cell strain Ab-1 with good binding and blocking activity in vitro was selected. The results are shown in Table 2.

TABLE 2

The activity of murine antibody in vitro

| candidate antibody | Test example 1- EC50 (nM) | Test example 2- IC50 (nM) |
|---|---|---|
| Ab-1 | 0.701 | 9.91 |

Example 4. Humanization of Murine Anti-Human Sclerostin Antibody

A monoclonal hybridoma cell strain Ab-1 with good bioactivity in vitro was selected, the hybridoma was sequenced, and humanization, recombinant expression and activity evaluation were further performed.

The process of hybridoma sequencing was performed as follows. The hybridoma cells were collected at logarithmic growth phase, and RNA was isolated in Trizol (Invitrogen 15596-018, according to the kit instructions), and then reverse transcription (PrimeScript™ Reverse Transcriptase, Takara, cat #2680A) of RNA was performed as instructed. The cDNAs obtained by reverse transcription were amplified by PCR using the mouse Ig-Primer Set (Novagen, TB326 Rev.B 0503) and sequenced by a sequencing company. The amino acid sequences corresponding to the obtained DNA sequences are shown as SEQ ID NO: 5 and SEQ ID NO: 6:

The heavy chain variable region obtained from Hybridoma cells:
(SEQ ID NO: 5)
EVQLQQSGPELVKPGTSVKIPCQTSGYTFTDYNLDWLKQRPGESLEWIGD
IDPNNGDILYNQKFRDKATLTVDTSSNTAYLELRSLTSEDTAVYYCARRW
AYYFDYWGQGTTLTISS The light chain variable region obtained from Hybridoma cells:
(SEQ ID NO: 6)
NTVMTQTPKLLFVSAGDRITITCKASQSVSNDVAWYQQKPGQSPKLLIYY
TSNRFTGVPDRFTGSGYGTDFTLTINTVQAEDLAVYFCQQDYSSPVTFGA
GTKLELK The humanization method of murine anti-human SOST monoclonal antibody was performed as disclosed in many literatures in the art. Briefly, the constant region domain of the parental (murine antibody) was replaced by a human constant region domain, and the human antibody germline was selected according to the homology between the murine and human antibody. The candidate molecules showing good activity in the present invention were humanized and the results are as follows.

1. The CDR Region of Murine Anti-Sclerostin Antibody

The amino acid residues of VH/VL CDR were identified and annotated by the Kabat numbering system.

The CDR sequences of murine Ab-1 of present invention are described in Table 3:

TABLE 3

The CDR sequences of murine anti-sclerostin antibody

| Antibody | Ab-1 |
|---|---|
| Heavy Chain CDR1 | DYNLD (SEQ ID NO: 7) |
| Heavy Chain CDR2 | DIDPNNGDILYNQKFRD (SEQ ID NO: 8) |
| Heavy Chain CDR3 | RWAYYFDY (SEQ ID NO: 9) |
| Light Chain CDR1 | KASQSVSNDVA (SEQ ID NO: 10) |
| Light Chain CDR2 | YTSNRFT (SEQ ID NO: 11) |
| Light Chain CDR3 | QQDYSSPVT (SEQ ID NO: 12) |

2. Selecting the Human Germline FR Region Sequence

On the basis of the typical VH/VL CDR structure of a murine antibody, the heavy and light chain variable region sequences were compared with the antibody Germline database, and a human germline template with high homology was selected, wherein the framework region of the human germline light chain came from the human kappa light chain gene, and preferably, IGKV1-39*01 or IGKV4-1*01 of the human germline light chain templates was selected in the present invention. The framework region of the human germline heavy chain came from the human heavy chain, and preferably, IGHV1-18*01 of the human germline heavy chain template was selected in the present invention. The CDR region of the murine antibody Ab-1 was transplanted into the selected humanized template, replacing the humanized variable region, and then recombined with the IgG constant region. Based on the three-dimensional structure of the murine antibody, back-mutations were performed on the entrapped residues, and on the residues that have direct interactions with the CDR regions, as well as optimizations of the residues that have important effects on the conformation of VL and VH, and the residues in the CDR region which exhibit chemical instability (the heavy chain CDR2 was optimized to obtain a new heavy chain CDR2 sequence DIDPNDGDILYNQKFRD, SEQ ID NO: 13), and the final humanized molecule was obtained. The heavy chain variable region sequences of the final humanized molecule are shown in SEQ ID NOs: 14-16, and these sequences can be combined with any one of the heavy chain constant regions shown in SEQ ID NOs: 20-22. The light chain variable region sequences of the final humanized molecule are shown in SEQ ID NOs: 17-19, and these sequences can be combined with the light chain constant region sequences shown in SEQ ID NO: 23, respectively.

1. Heavy chain variable region:

```
Heavy chain variable region of Ab-5:
                                       (SEQ ID NO: 14)
EVQLVQSGAEVKKPGASVKVSCKASGYTFTDYNLDWLRQAPGEGLEWIGD
IDPNDGDILYNQKFRDRVTMTTDTSTSTAYMELRSLRSDDTAVYYCARRW
AYYFDYWGQGTTVTVSS Heavy chain variable region of Ab-9:
                                       (SEQ ID NO: 15)
EVQLVQSGAEVKKPGASVKVSCKASGYTFTDYNLDWLRQAPGEGLEWIGD
IDPNNGDILYNQKFRDRVTMTTDTSTSTAYMELRSLRSDDTAVYYCARRW
AYYFDYWGQGTTVTVSS Heavy chain variable region of Ab-10:
                                       (SEQ ID NO: 16)
EVQLVQSGAEVKKPGASVKVSCKASGYTFTDYNLDWVRQAPGQGLEWMGD
IDPNNGDILYNQKFRDRVTMTTDTSTSTAYMELRSLRSDDTAVYYCARRW
AYYFDYWGQGTTVTVSS
```

2. The heavy chain constant region of each antibody can be any one of the following sequences:

```
The heavy chain constant region of human IgG4
(K amino acid residues were deleted):
                                       (SEQ ID NO: 20)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQEDP

EVQFNWYVDGVEVHNAKTKPREEQFNSTYRVVSVLTVLHQDWLNGKEYKC

KVSNKGLPSSIEKTISKAKGQPREPQVYTLPPSQEEMTKNQVSLTCLVKG

FYPSDIAVEWESNGQPENNYKTIPPVLDSDGSFFLYSRLTVDKSRWQEGN

VFSCSVMHEALHNHYTQKSLSLSLG
```

```
The heavy chain constant region of human IgG4:
                                       (SEQ ID NO: 21)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQEDP

EVQFNWYVDGVEVHNAKTKPREEQFNSTYRWSVLTVLHQDWLNGKEYKCK

VSNKGLPSSIEKTISKAKGQPREPQVYTLPPSQEEMTKNQVSLTCLVKGF

YPSDIAVEWESNGQPENNYKTTPPVLDSDGSFFLYSRLTVDKSRWQEGNV

FSCSVMHEALHNHYTQKSLSLSLGK

The heavy chain constant region of human IgG2:
                                       (SEQ ID NO: 22)
ASTKGPSVFPLAPSSKSTSGGTAALGCLVKDYFPEPVTVSWNSGALTSGV

HTFPAVLQSSGLYSLSSWTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRWSVLTVLHQDWLNGKEY

KCKVSNKALPAPIEKTISKAKGQPREPQVYTLPPSRDELTKNQVSLTCLV

KGFYPSDIAVEWESNGQPEKNYKTTPPVLDSDGSFFLYSKLTVDKSRWQQ

GNVFSCSVMHEALHNHYTQKSLSLSPGK
```

3. Light chain variable region:

```
The light chain variable region of Ab-5:
                                       (SEQ ID NO: 17)
DIVMTQSPSSLSASVGDRVTITCKASQSVSNDVAWYQQKPGKSPKLLIYY
TSNRFTGVPDRFSGSGSGTDFTLTISSLQPEDFATYFCQQDYSSPVTFGG
GTKVEIK The light chain variable region of Ab-9:
                                       (SEQ ID NO: 18)
NIVMTQSPSSLSASVGDRVTITCKASQSVSNDVAWYQQKPGKSPKLLIYY
TSNRFTGVPDRFSGSGSGTDFTLTISSLQPEDFATYFCQQDYSSPVTFGG
GTKVEIK The light chain variable region of Ab-10:
                                       (SEQ ID NO: 19)
DIQMTQSPSSLSASVGDRVTITCKASQSVSNDVAWYQQKPGKAPKLLIYY
TSNRFTGVPSRFSGSGSGTDFTLTISSLQPEDFATYYCQQDYSSPVTFGG
GTKVEIK
```

4. The light chain constant region came from human k chain:

```
                                       (SEQ ID NO: 23)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC
```

The antibodies were cloned, expressed and purified by gene cloning and recombinant expression, and then detected by binding ELISA assay (Test Example 1 and Test Example 3), blocking assay of the binding between antigen and receptor (Test Example 2), Biacore (Test Example 4), cell activity detection (Test Example 5) etc. Finally, the humanized antibodies Ab-5, Ab-9, and Ab-10 with the best activity were selected, and the sequences are shown as follows:

```
Humanized antibody Ab-10:
Heavy chain:
                                       (SEQ ID NO: 24)
EVQLVQSGAEVKKPGASVKVSCKASGYTFTDYNLDWVRQAPGQGLEWMGD

IDPNNGDILYNQKFRDRVTMTTDTSTSTAYMELRSLRSDDTAVYYCARRW

AYYFDYWGQGTTVTVSSASTKGPSVFPLAPSSKSTSGGTAALGCLVKDYF
```

-continued
PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVWDVSHEDPEVKFNWYVDGVEVHNAKTKPREEQYNSTYR

WSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK

Light chain:
(SEQ ID NO: 27)
DIQMTQSPSSLSASVGDRVTITCKASQSVSNDVAWYQQKPGKAPKLLIYY

TSNRFTGVPSRFSGSGSGTDFTLTISSLQPEDFATYYCQQDYSSPVTFGC

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Humanized antibody Ab-9:
Heavy chain:
(SEQ ID NO: 25)
EVQLVQSGAEVKKPGASVKVSCKASGYTFTDYNLDWLRQAPGEGLEWIGD

IDPNNGDILYNQKFRDRVTMTTDTSTSTAYMELRSLRSDDTAVYYCARRW

AYYFDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRWSV

LTVLHQDWLNGKEYKCKVSNKGLPSSIEKTISKAKGQPREPQVYTLPPSQ

EEMTKNQVSLTCLVKGFYPSDIAVEWESNGQPENNYKTTPPVLDSDGSFF

LYSRLTVDKSRWQEGNVFSCSVMHEALHNHYTQKSLSLSLGK

Light chain:
(SEQ ID NO. 28)
NIVMTQSPSSLSASVGDRVTITCKASQSVSNDVAWYQQKPGKSPKLLIYY

TSNRFTGVPDRFSGSGSGTDFTLTISSLQPEDFATYFCQQDYSSPVTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Humanized antibody Ab-5:
Heavy chain:
(SEQ ID NO: 26)
EVQLVQSGAEVKKPGASVKVSCKASGYTFTDYNLDWLRQAPGEGLEWIGD

IDPNDGDILYNQKFRDRVTMTTDTSTSTAYMELRSLRSDDTAVYYCARKW

AYYFDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRWS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLG

-continued
Light chain:
(SEQ ID NO: 29)
DIVMTQSPSSLSASVGDRVTITCKASQSVSNDVAWYQQKPGKSPKLLIYY

TSNRFTGVPDRFSGSGSGTDFTLTISSLQPEDFATYFCQQDYSSPVTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The binding activity data between the humanized anti-human SOST antibody and human sclerostin (h-SOST-Flag) in the present invention are shown in Table 4.

TEST EXAMPLES

Bioactivity Evaluation In Vitro

Test Example 1: Binding ELISA Assay

The sclerostin antibody blocks the binding of sclerostin with its receptor on the cell membrane, thereby blocking the downstream signaling pathway of sclerostin. ELISA experiments were used to detect the binding properties of sclerostin antibodies. Sclerostin with a Flag tag (h-SOST-FLAG, encoded by SEQID NO: 2) was biotinylated with a biotin labeling kit (Dojido Chem, LK03), and immobilized onto a 96-well EIA/RIA plate via binding to streptavidin coated on it. After the antibody was added, the strength of the signal was used to determine the binding activity between the antibody and human sclerostin.

Streptavidin (Sigma, S4762-5MG) was diluted to a concentration of 5 µg/ml with PBS buffer at pH 7.4 (Sigma, P4417-100TAB), and added to a 96-well EIA/RIA plate (Corning, CLS3590-100EA) at a volume of 50 µl/well. Then, the plate was incubated in an incubator at 37° C. for 2 hours. The liquid was discarded, the plates were blocked with 200 µl/well of blocking solution containing 5% skim milk (Guangming skim milk) in PBS, and incubated in an incubator at 37° C. for 2.5 hours or overnight (16-18 hours) at 4° C. After blocking, the blocking solution was discarded and the plate was washed 5 times with PBST buffer (pH 7.4 PBS containing 0.05% tween-20). Biotinylated SOST-FLAG protein (R&D SYSTEM, 1505-LR-025) was diluted with sample dilution buffer (pH 7.4 PBS containing 1% BSA) to 0.5 µg/ml and was added to each well at 50 µl/well, then the plate was incubated in the incubator at 37° C. for 2 hours. After incubation, the reaction solution in the plate was discarded, and the plate was washed with PBST 6 times, and then 50 µl/well of gradient dilution antibody with sample dilution buffer was added, and the plate was incubated in a incubator at 37° C. for 2 hours. The plate was washed 6 times with PBST after incubation, added with 100 µl/well of HRP-labeled goat anti-mouse (Jackson Immuno Research, Cat No. 115-035-003) or HRP-labeled goat anti-human secondary antibody (Jackson Immuno Research, Cat No. 109-035-003) diluted in sample dilution, and incubated at 37° C. for 1 hour. After washing the plates with PBST 6 times, 50 µl/well of TMB substrate (KPL, Cat No. 52-00-03) was added to each well, and incubated at room temperature for 10-15 min, and the reaction was stopped by adding 50 µl 1M $H_2SO_4$ to each well. The OD value at a wavelength of 450 nm was read on a NOVOStar microplate reader, and then $EC_{50}$ values of the binding between the sclerostin antibody of the present invention and human sclerostin were calculated. The results are shown in Table 4.

TABLE 4

The binding activity between humanized anti-SOST
antibody and human sclerostin (h-SOST-Flag)

| Test Antibody | EC50(nM) |
|---|---|
| Ab-1 | 0.701 |
| Ab-5 | 0.63 |
| Ab-9 | 0.4 |
| Ab-10 | 0.54 |

The results showed that the humanized anti-human SOST antibodies of the present invention maintain the same binding activity as the corresponding parental antibody.

Test Example 2: An Assay of Anti-SOST Antibody Blocking the Binding of Sclerostin with LRP-6

Sclerostin can inhibit the activity of the wnt/β-catenin signaling pathway through binding with co-receptor LRP5/LRP-6 of the wnt/β-catenin signaling pathway on the cell membrane, to block osteogenesis. In this experiment, the activity of screened anti-human SOST antibody in blocking the binding between human SOST/monkey SOST and human LRP-6 was detected using an in vitro blocking assay. The positive control was Romosozumab (the preparation method was as described in reference WHO Drug Information, Vol. 25, No. 4, 2011, 413-465, P434).

In the method, goat anti-human Fc antibody was coated onto a 96-well EIA/RIA plate, and then LRP-6-Fc fusion protein was added for incubation. The biotinylated sclerostin protein and the anti-sclerostin antibody were co-incubated, and then added to the plate for incubation. After washing the plate, the binding amount between biotinylated sclerostin and LRP-6 was measured, and the $IC_{50}$ value of the blocking activity of the sclerostin antibody was calculated.

The goat anti-human Fc antibody was diluted to a concentration of 1 µg/ml with PBS buffer at pH 7.4 (Sigma, P4417-100TAB), and added to a 96-well EIA/RIA plate at a volume of 100 µl/well. Then, the plate was incubated at 37° C. for 2 hours. After discarding the liquid, the plates were blocked with 200 µl/well of blocking solution containing 5% skim milk (Guangming skim milk) in PBS, and incubated at 37° C. for 2.5 hours. After blocking, the blocking solution was discarded and the plate was washed 5 times with PBST buffer (pH 7.4 PBS containing 0.05% tween-20). LPR-6-Fc fusion protein (R&D SYSTEM, 1505-LRP-025) was diluted with sample dilution buffer (pH 7.4 PBS containing 1% BSA) to 1 µg/ml and 50 µl/well was added, then the plate was incubated at 37° C. for 2 hours. The human sclerostin protein (R&D SYSTEM, 1406-ST/CF) at a concentration of 1.12 µg/ml was labeled by using a biotin labeling kit (Dojido Chemical, LK03), and was added to the dilution plate at a volume of 30 µl/well. Then, 30 µl/well of test sclerostin antibody diluted to the appropriate concentration was added to each well, then the plate was mixed and incubated in the incubator at 37° C. for 2 hours. After incubation, the reaction solution in the plate was discarded. The plate was washed with PBST 6 times, and then the antigen and antibody mixture in the dilution plate was added to the plate and incubated at 4° C. overnight (16-18 hours). The solution in the plate was discarded, and the plate was washed 6 times with PBST. Then, 50 µl/well of Streptavidin-Peroxidase Polymer (Sigma, 52438-250UG), which had been diluted with sample dilution buffer at ratio of 1:600, was added to each well, and the plate was incubated at 37° C. for 1 hour. After washing the plates 6 times with PBST, 50 µl/well of TMB substrate (KPL, Cat No. 52-00-03) was added to each well, and incubated at room temperature for 3-10 min, and the reaction was stopped by the addition of 50 µl 1M $H_2SO_4$ to each well. The OD value at a wavelength of 450 nm was read on a NOVOStar microplate reader, and then $IC_{50}$ values of sclerostin antibody in blocking the binding between human sclerostin and LRP-6 were calculated. The results are shown in Table 5.

The above method was used to detect the $IC_{50}$ values of the sclerostin antibody of the present invention in blocking the binding between monkey sclerostin (encoded and expressed by SEQ ID NO: 4 and then purified) and LRP-6. The results are shown in Table 5.

TABLE 5

The activity of the humanized SOST antibody of
the present invention in blocking the binding between
sclerostin of different species and LRP-6

| | IC50 (nM) | |
|---|---|---|
| Test Antibody | Human sclerostin | Monkey sclerostin |
| Ab-5 | 23.5 | 110.3 |
| Romosozumab | 27.9 | 46.8 |

Note:
N/A indicates not detected.

The results show that the blocking activity of humanized anti-human SOST antibody of the present invention in blocking the binding between human/monkey sclerostin and LRP-6 is comparable to that of the positive antibody Romosozumab.

Test Example 3: Biacore Determination

The Biacore (GE) was used to determine the affinity of humanized anti-SOST antibody with human, monkey, and murine SOST.

The anti-human capture antibody was covalently linked to the CMS biosensor chip (Cat. #BR-1000-12, GE) of a Biacore instrument (Biacore X100, GE) according to the method described in the instructions of anti-human trapping kit (GE, Cat.# BR-1008-39) for affinity capturing an amount of a test antibody. Then, a gradient of concentrations of SOST antigen (human SOST, R&D SYSTEM, Cat.#1406-ST-025/CF, R&D; monkey SOST, cyno-SOST-Flag, obtained by purification, encoded by SEQ ID NO: 4 of Example 1; murine SOST, m-SOST-Flag, obtained by purification, encoded by SEQ ID NO: 3 of Example 1) were flowed through the surface of the biochip. The reaction signal was detected in real-time using a Biacore instrument (GE, BiacoreX100) to obtain the association and dissociation curves. After each cycle of dissociation was finished in the experiment, the biochip was washed and regenerated with regeneration solution in the anti-human capture kit. The amino-coupled kit used in the experiments was purchased from GE (Cat. #BR-1000-50, GE), and the buffer was HBS-EP+10× buffer solution (Cat. #BR-1006-69, GE), and the buffer was diluted to 1× (pH 7.4) with D.I. Water.

The data obtained was fitted by GE BIAevaluation version 4.1 software using a 1:1 Langmuir model, and the affinity value was generated. The results are shown in Table 6.

TABLE 6

The in vitro activity of humanized antibody
against sclerostin of different species

| Test SOST antibody | Human SOST $K_D$ (nM) | Monkey SOST $K_D$ (nM) |
|---|---|---|
| Ab-5 | 0.064 | 0.030 |
| Romosozumab | 0.67 | 0.52 |

Note: no indicates blocking activity was not detected.

The humanized antibody Ab-5 in the present invention has high affinity for human SOST and monkey SOST, and such affinity is greater than 10 times higher as compared to the positive molecule.

Test Example 4: Activity Test of Anti-Sclerostin Antibody on Cell

In this study, the in vitro activity of the SOST antibody of the present invention on cells was evaluated according to an $EC_{50}$ value obtained by detecting the activity of alkaline phosphatase (ALP) in cells.

C2C12 cells (Chinese Academy of Sciences, cell bank, Catalog #GNM26) were cultured in DMEM medium containing 10% FBS, and passaged 2 to 3 times a week at a ratio of 1:5 or 1:10. During the passage, the culture medium was discarded and 5 mL of 0.25% trypsin was used to wash the cell layer, and then the trypsin was removed. The cells were digested in an incubator for 3-5 minutes and resuspended in fresh medium. Then, 100 µL of cell suspension was added to a 96-well cell culture plate at a density of $5 \times 10^4$ cell/ml, the medium was DMEM containing 10% FBS, and only 100 µl of DMEM medium containing 10% FBS was added to the outside of the 96-well plate. Then, the culture plates were cultured in an incubator for 24 hours (37° C., 5% $CO_2$). Once cell adherence was observed, the medium was discarded; and 70 µl of DMEM medium containing 10% FBS was added to each well. Then, 10 µl of wnt3a (R&D, Catalog #5036-WN-010) at a final concentration of 100 ng/ml and SOST (R&D, Catalog #1406-ST-025) at a final concentration of 5 µg/ml were added to each well, respectively. The test samples were diluted with PBS into different concentration gradients, and 10 µl of different concentrations of the test sample were added to the culture plate. Then, the culture plate was incubated in an incubator for three days (37° C., 5% $CO_2$). The medium was discarded, and 150 µl of ALP substrate was added to each well, and the culture plate was incubated in an incubator for 2 hours. The OD value at a wavelength of 450 nm was read on microplate reader (PerkinElmer, Catalog# VICTOR[3]), and then $EC_{50}$ values were calculated. The results are shown in Table 7.

TABLE 7

Activity test of an antibody of the present invention on cells

| Test SOST antibody | Cell activity EC50 (nM) |
|---|---|
| Ab-5 | 84.7 |
| Romosozumab | 71.6 |

The results showed that the activity of humanized SOST antibody Ab-5 of the present invention acting on cells is comparable to that of the positive antibody Romosozumab.

Pharmacokinetic Evaluation

Test Example 5: Evaluation of the $T_{1/2}$ of Humanized Anti-SOST Antibody in Cynomolgus Monkey Three cynomolgus monkeys used in experiment were female, 4-5 years old, less than 4 kg, and were purchased from Guangxi Guidong Primate Breeding Development Co., Ltd. Feeding environment: common room. After the cynomolgus monkeys were purchased, each monkey was kept in a separate cage, and the monkeys were given ad libitum access to water and diet. The duration for adaption in the laboratory environment was not less than 14 days, with 12/12 hour light/dark cycle regulation, at a temperature of 23-29° C. and relative humidity of 40-70%. Three cynomolgus monkeys were numbered before starting the experiment. On the day of experiment, each cynomolgus monkey was injected subcutaneously with the test drug or positive molecule (30 mg/kg) at 8 ml/monkey/administration.

The monkeys were fixed on a monkey chair and the blood was taken via elbow vein or saphenous vein (about 1.5 mL of blood each sampling) to obtain serum, which was preserved at −20 degrees Celsius. Blood sampling time points were 12 hours before administration, and 1 hour, 2 hours, 4 hours, 8 hours, 12 hours, and 24 hours (second day) after administration at the first day, the third day, fifth day, seventh day, fourteenth day, twenty-first day and twenty-eighth day. After the blood samples were collected, the serum concentration of the drug was detected by ELISA and PK analysis was performed. The results are shown in Table 8.

TABLE 8

The $T_{1/2}$ of humanized anti-SOST antibody in cynomolgus monkey

| Test Drug | T½ (Days) |
|---|---|
| Ab-5 | 8.66 |
| Romosozumab | 4.78 |

The results showed that the humanized candidate molecules have a longer half-life in cynomolgus monkey in vivo, which is about two times (Ab-5) greater than that of the positive molecule Romosozumab.

Evaluation of Biology Activity In Vivo

Test Example 6: Evaluation of the Efficacy In Vivo of Humanized Anti-SOST Antibody in Cynomolgus Monkey Three cynomolgus monkeys used in the experiment were female, 4-5 years old, less than 4 kg, and were purchased from Guangxi Guidong Primate Breeding Development Co., Ltd. Feeding environment: common room. After the cynomolgus monkeys were purchased, each monkey was kept in a separate cage and the monkeys were given ad libitum access to water and diet. The duration for adaption in the laboratory environment was not less than 14 days, with 12/12 hour light/dark cycle regulation, at a temperature of 23-29° C. and relative humidity of 40-70%. Three cynomolgus monkeys were numbered one day before starting the experiment, and then the blood was taken after anesthesia to obtain serum and plasma, and the bone mineral density and bone mineral content of lumbar and distal radius were tested. The resulting values were used as the base values. Each cynomolgus monkey was injected subcutaneously with test drug (10, 30, 60 mg/kg, different doses) and positive molecules (30 mg/kg) at 8 ml/monkey/administration. The drugs were administered once a month for a total of 2 times. During the experiment, in the fourth and eighth week after the administration, the animals were tested for bone mineral density and bone mineral content of the lumbar vertebrae and the distal radius, respectively.

Two months after the experiment, all animals were anesthetized and euthanized (with excess dose of pentobarbital sodium). After that, the bone mineral density and bone mineral content of the second to the fifth lumbar and distal radius were tested.

Figure 2:
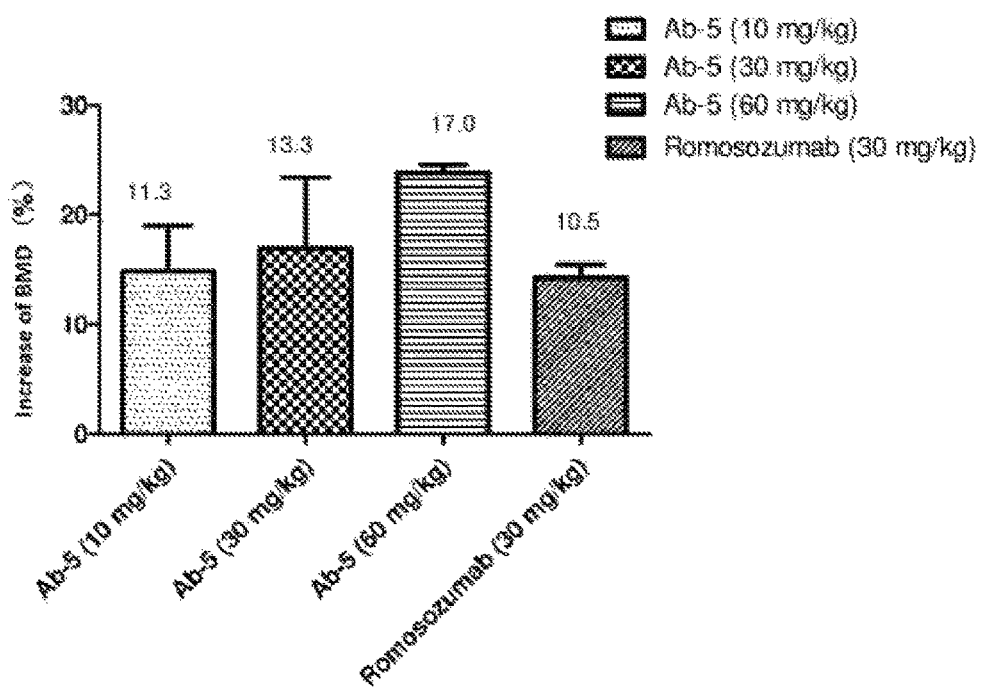
FIG. 2 shows the percent increase in lumbar vertebrae bone mineral density (BMD) obtained by using the humanized anti-SOST antibody of the present invention. The results show that the efficacy of the humanized anti-SOST antibody of the present invention was dose-dependent in cynomolgus monkey. The humanized anti-SOST antibody Ab-5 has an efficacy of 10 mg/kg, which is compared to 30 mg/kg of the positive molecule. This means that the efficacy in monkey of the molecule of the present invention was three times as much as that of the positive molecule Romosozumab.

The results are shown in Table 9, FIG. 1 and FIG. 2.

TABLE 9

Efficacy of anti-human SOST antibody in cynomolgus monkey

| Test molecule | Dosage of administration (mg/kg) | Bone density change in the first month (%) | Bone density change in the second month (%) |
|---|---|---|---|
| Ab-5 | 10 | 4.89 ± 1.17 | 11.3 ± 4.6 |
|  | 30 | 8.98 ± 4.68 | 13.3 ± 7.0 |
|  | 60 | 7.44 ± 1.44 | 17.0 ± 1.1 |
| Romosozumab | 30 | 3.94 ± 2.36 | 10.5 ± 1.2 |

The results show that the in vivo efficacy of humanized anti-SOST antibody in the present invention was dose-dependent in cynomolgus monkey. The efficacy of humanized anti-SOST antibody Ab-5 at 10 mg/kg was equal to the positive molecule at 30 mg/kg (FIG. 2). This means that the efficacy of humanized anti-SOST antibody in the present invention is two times higher than that of the positive molecule Romosozumab in monkeys. When administered at the same dose, the $AUC_{0-t}$ (mg/ml*day) of the humanized antibody was 22.3, which is more than 2 times as much as that of the positive antibody Romosozumab (9.95) (see FIG. 1).

Solubility Test

Test Example 7: Solubility of Humanized Anti-SOST Antibody

To detect the solubility of humanized anti-SOST antibody, the antibody Ab-5 and the positive antibody Romosozumab with a gradient of increasing concentrations were detected for their contents of soluble antibody monomers, precipitation, and polymer content. In the test, the starting concentration of antibody was 10 mg/ml, which was dissolved in PBS buffer of pH 7.4. The samples were centrifuged in an ultrafiltration concentrator (Millipore, Amicon Ultra-15 50K) at 4 degrees Celsius, at 4000 rpm. During centrifugation, samples were taken at an interval of 5-10 minutes and the concentration of antibody was detected until it reached 30 mg/ml and 90 mg/ml. Samples under different concentration conditions were taken and subjected to SEC-HPLC analysis, respectively. The results are shown in Table 10.

TABLE 10

The solubility of anti-SOST antibody

| Antibody | Concentration (mg/ml) | Monomer (%) | Precipitation |
|---|---|---|---|
| Romosozumab | 10 | 95.8 | None |
| Romosozumab | 30 | 95.2 | None |
| Romosozumab | 90 | 92.0 | Mass Precipitation, turbidity |
| Ab-5 | 10 | 96.5 | None |
| Ab-5 | 30 | 96.6 | None |
| Ab-5 | 90 | 96.1 | None |

The above results showed that, when the antibody concentration of the invention was up to 90 mg/ml, it was still clear without precipitation, and the amount of antibody monomer did not change. However, the positive molecules at the same concentration had mass precipitation, and the amount of antibody monomer was reduced from 95.8% to 92%.

Stability Evaluation

Test Example 8: The Stability of Humanized Anti-SOST Antibody

To test the stability of the humanized anti-SOST antibody of the present invention, the antibody Ab-5 and the positive antibody Romosozumab were placed in PBS buffer at pH 7.4 at 4 degrees Celsius for 7 days. Two methods were used to detect the stability: one was to assess the amount of the formation of insoluble precipitate, which is visible to the naked eye, and the change of insoluble precipitation concentration before and after placement is calculated; and the other method was to test the changes in the content of soluble antibody monomers in the sample by SEC-HPLC. The initial antibody concentration was 30 mg/ml, which was the highest soluble concentration that the positive antibody could reach. The results are shown in Table 11.

TABLE 11

The Stability of anti-SOST antibody

| Anitbody | Changes of antibody concentration | | | Soluble monomers (%) | | Solution observation |
|---|---|---|---|---|---|---|
|  | Day 0 (mg/ml) | Day 7 (mg/ml) | Precipitation (%) | Day 0 | Day 7 | Day 7 |
| Romosozumab | 29 | 23.4 | 19.3 | 95.2 | 94.4 | Turbidity; Precipitation |
| Ab-5 | 31 | 31.1 | −0.3 | 96.6 | 96.4 | Clear and no precipitation |

The above results show that the positive antibody had 19.3% precipitation formed and a decrease in the amount of the antibody monomers was observed after 7 days of placement, even if the positive antibody does not precipitate at the starting point of its achievable concentration (30 mg/ml). In contrast, the antibody of the present invention was very stable without any precipitation and the solution was clear.

Considering the solubility and stability results, the antibody of the present invention has better performance than the positive antibody in the aspect of antibody preparation. It can be made at a high concentration, such as 90 mg/ml, and is still stable.

The invention claimed is:

1. An antibody or antigen-binding fragment thereof that specifically binds to human sclerostin, comprising:
   (I) a heavy chain variable region comprising a heavy chain complementarity determining region 1 (CDR1), a heavy chain CDR2, and a heavy chain CDR3 having the amino acid sequences of SEQ ID NO: 7, SEQ ID NO: 8, and SEQ ID NO: 9, respectively; and
   a light chain variable region comprising a light chain CDR1, a light chain CDR2, and a light chain CDR3 having the amino acid sequences of SEQ ID NO: 10, SEQ ID NO: 11, and SEQ ID NO: 12, respectively; or
   (II) a heavy chain variable region comprising a heavy chain CDR1, a heavy chain CDR2, and a heavy chain CDR3 having the amino acid sequences of SEQ ID NO: 7, SEQ ID NO: 13, and SEQ ID NO: 9, respectively; and
   a light chain variable region comprising a light chain CDR1, a light chain CDR2, and a light chain CDR3 having the amino acid sequences of SEQ ID NO: 10, SEQ ID NO: 11, and SEQ ID NO: 12, respectively.

2. The antibody or antigen-binding fragment thereof that specifically binds to human sclerostin according to claim 1, wherein the antibody or the antigen-binding fragment thereof is a murine antibody or fragment thereof.

3. The antibody or antigen-binding fragment thereof that specifically binds to human sclerostin according to claim 2, wherein the heavy chain variable region sequence of the murine antibody comprises SEQ ID NO: 5, or a sequence having at least 95% identity to SEQ ID NO: 5.

4. The antibody or antigen-binding fragment thereof that specifically binds to human sclerostin according to claim 2, wherein the light chain variable region sequence of the murine antibody comprises SEQ ID NO: 6, or a sequence having at least 95% identity to SEQ ID NO: 6.

5. The antibody or antigen-binding fragment thereof that specifically binds to human sclerostin according to claim 1, wherein the antibody or the antigen-binding fragment thereof is a chimeric antibody or humanized antibody, or a fragment thereof.

6. The antibody or antigen-binding fragment thereof that specifically binds to human sclerostin according to claim 5 being a humanized antibody, wherein the humanized antibody comprises framework regions FR1, FR2, FR3, and FR4 of human germline heavy chain IGHV1-18*01, or a mutant sequence thereof.

7. The antibody or antigen-binding fragment thereof that specifically binds to human sclerostin according to claim 6, wherein the humanized antibody comprises a heavy chain variable region comprising an amino acid sequence selected from the group consisting of SEQ ID NOs: 14-16, a mutant sequence thereof, and sequences having at least 95% identity to SEQ ID NOs: 14-16.

8. The antibody or antigen-binding fragment thereof that specifically binds to human sclerostin according to claim 5 being a humanized antibody, wherein the humanized antibody comprises framework regions FR1, FR2, FR3, and FR4 of human germline light chain IGK V1-39*01 or IGK V4-1*01, or a mutant sequence thereof.

9. The antibody or antigen-binding fragment thereof that specifically binds to human sclerostin according to claim 8, wherein the humanized antibody comprises a light chain variable region having an amino acid sequence selected from the group consisting of SEQ ID NOs: 17-19, a mutant sequence thereof, and sequences having at least 95% identity to SEQ ID NOs: 17-19.

10. The antibody or antigen-binding fragment thereof that specifically binds to human sclerostin according to claim 5 being a humanized antibody, wherein the humanized antibody comprises:
 a heavy chain variable region sequence of SEQ ID NO: 14 and a light chain variable region sequence of SEQ ID NO: 17;
 a heavy chain variable region sequence of SEQ ID NO: 15 and a light chain variable region sequence of SEQ ID NO: 18; or
 a heavy chain variable region sequence of SEQ ID NO: 16 and a light chain variable region sequence of SEQ ID NO: 19.

11. The antibody or antigen-binding fragment thereof that specifically binds to human sclerostin according to claim 5, wherein the heavy chain constant region of the humanized antibody comprises a constant region derived from human IgG1 or a variant thereof, human IgG2 or a variant thereof, human IgG3 or a variant thereof, or human IgG4 or a variant thereof.

12. The antibody or antigen-binding fragment thereof that specifically binds to human sclerostin according to claim 11, comprising a full-length heavy chain sequence selected from the group consisting of SEQ ID NOs: 24-26 and sequences having at least 90% identity to SEQ ID NOs: 24-26.

13. The antibody or antigen-binding fragment thereof that specifically binds to human sclerostin according to claim 5, wherein the light chain constant region of the humanized antibody comprises a constant region selected from the group consisting of human κ and human λ, or a variant thereof.

14. The antibody or antigen-binding fragment thereof that specifically binds to human sclerostin according to claim 13, comprising a full-length light chain sequence selected from the group consisting of SEQ ID NOs: 27-29 and sequences having at least 90% identity to SEQ ID NOs: 27-29.

15. The antibody or antigen-binding fragment thereof that specifically binds to human sclerostin according to claim 5, comprising:
 a full-length heavy chain sequence of SEQ ID NO: 24 and a full-length light chain sequence of SEQ ID NO: 27;
 a full-length heavy chain sequence of SEQ ID NO: 25 and a full-length light chain sequence of SEQ ID NO: 28; or
 a full-length heavy chain sequence of SEQ ID NO: 26 and a full-length light chain sequence of SEQ ID NO: 29.

16. A pharmaceutical composition, comprising the antibody or antigen-binding fragment thereof according to claim 1, and one or more pharmaceutically acceptable excipients, diluents or carriers.

17. A pharmaceutical composition, comprising the antibody or antigen-binding fragment thereof according to claim 15, and one or more pharmaceutically acceptable excipients, diluents or carriers.

18. A method of increasing at least one of bone mass, bone mineral density, bone mineral content, and bone strength in a subject in need thereof, the method comprising administering to the subject the pharmaceutical composition according to claim 16.

19. A method of treating a sclerostin (SOST)-mediated bone disease or disorder in a subject in need thereof, the method comprising administering to the subject the pharmaceutical composition according to claim 16, wherein the SOST-mediated bone disease or disorder is selected from the group consisting of osteoporosis, osteopenia, osteoarthritis, rheumatoid arthritis, periodontal disease, and multiple myeloma.

20. A method of increasing at least one of bone mass, bone mineral density, bone mineral content, and bone strength in a subject in need thereof, or a method of treating a sclerostin (SOST)-mediated bone disease or disorder in a subject in need thereof, wherein the SOST-mediated bone disease or disorder is selected from the group consisting of osteoporosis, osteopenia or osteoarthritis, rheumatoid arthritis, periodontal disease, and multiple myeloma, the method comprising administering to the subject the pharmaceutical composition according to claim 17.

* * * * *